US011039764B2

(12) United States Patent
Reid et al.

(10) Patent No.: US 11,039,764 B2
(45) Date of Patent: Jun. 22, 2021

(54) BIOMETRIC IDENTIFICATION IN MEDICAL DEVICES

(71) Applicant: ZOLL Medical Corporation, Chelmsford, MA (US)

(72) Inventors: C. Shane Reid, Boulder, CO (US); Mark Weary, Billerica, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 185 days.

(21) Appl. No.: 15/468,431

(22) Filed: Mar. 24, 2017

(65) Prior Publication Data

US 2017/0296107 A1    Oct. 19, 2017

Related U.S. Application Data

(60) Provisional application No. 62/315,833, filed on Mar. 31, 2016.

(51) Int. Cl.
  *A61B 5/1171* (2016.01)
  *A61B 5/1172* (2016.01)
  (Continued)

(52) U.S. Cl.
  CPC .......... *A61B 5/1171* (2016.02); *A61B 5/002* (2013.01); *A61B 5/0006* (2013.01);
  (Continued)

(58) Field of Classification Search
  CPC ..... A61B 5/117; A61B 5/1171; A61B 5/1176; A61B 5/1172; A61B 5/02438;
  (Continued)

(56) References Cited

U.S. PATENT DOCUMENTS 5,071,168 A    12/1991  Shamos
6,128,530 A *  10/2000  Galen .................. A61N 1/3931
                                                                607/5
(Continued)

FOREIGN PATENT DOCUMENTS

DE    202005008825 U1    9/2005
KR       20090092445 A    9/2009
(Continued)

OTHER PUBLICATIONS

"Biometrics in Healthcare," VAR Insights, downloaded from internet https://www.varinsights.com/doc/biometrics-in-healthcare-0001 <http://www.varinsights.com/doc/biometrics-in-healthcare-0001> Oct. 24, 2017, (3 pages).

*Primary Examiner* — Nathan J Jenness
(74) *Attorney, Agent, or Firm* — Finch & Maloney PLLC

(57) ABSTRACT

The present disclosure describes systems, apparatus, and methods for collecting biometric data from a patient. In some cases, this biometric data can be collected during the course of an emergency encounter using a medical device. The medical device can also perform other functions, such as monitor patient vital signs, receive and record notes and textual information, communicate with other devices, and/or deliver a therapeutic treatment. The medical device can also be configured to record and/or maintain a patient record, and to embed the patient biometric data into the patient record for use in later confirming and/or determining an identity of the patient. Some embodiments can also collect biometric data relating to one or more caregivers of the patient, and to embed the caregiver biometric data into the patient record. This caregiver biometric data can be used to confirm and/or identify one or more caregivers in a patient record.

24 Claims, 7 Drawing Sheets

(51) Int. Cl.
| | | |
|---|---|---|
| *A61B 5/00* | (2006.01) | |
| *A61N 1/39* | (2006.01) | |
| *G06K 9/00* | (2006.01) | |
| *G16H 20/40* | (2018.01) | |
| *G16H 10/60* | (2018.01) | |
| *A61B 5/024* | (2006.01) | |
| *A61B 8/00* | (2006.01) | |
| *A61B 5/145* | (2006.01) | |
| *A61M 16/00* | (2006.01) | |
| *G16H 50/30* | (2018.01) | |
| *G16H 40/63* | (2018.01) | |
| *A61B 5/25* | (2021.01) | |
| *A61B 5/0205* | (2006.01) | |
| *A61M 16/04* | (2006.01) | |
| *A61B 7/00* | (2006.01) | |

(52) U.S. Cl.
CPC ........ *A61B 5/0022* (2013.01); *A61B 5/02438* (2013.01); *A61B 5/1172* (2013.01); *A61B 5/1176* (2013.01); *A61B 5/14542* (2013.01); *A61B 5/25* (2021.01); *A61B 5/4836* (2013.01); *A61B 8/44* (2013.01); *A61M 16/0003* (2014.02); *A61N 1/3904* (2017.08); *A61N 1/3925* (2013.01); *A61N 1/3987* (2013.01); *A61N 1/3993* (2013.01); *G06K 9/00892* (2013.01); *G16H 10/60* (2018.01); *G16H 20/40* (2018.01); *G16H 40/63* (2018.01); *G16H 50/30* (2018.01); *A61B 5/02055* (2013.01); *A61B 7/00* (2013.01); *A61B 2505/01* (2013.01); *A61B 2560/0462* (2013.01); *A61B 2562/0204* (2013.01); *A61B 2562/0219* (2013.01); *A61M 16/04* (2013.01); *A61M 2205/6009* (2013.01); *A61M 2205/609* (2013.01)

(58) Field of Classification Search
CPC ... A61B 5/0022; A61B 5/002; A61B 5/14542; A61B 5/4836; A61B 5/02055; A61B 2505/01; G16H 40/63; G16H 10/60; G16H 20/40; G16H 50/30; A61N 1/3904; A61N 1/3993; A61N 1/3925; A61N 1/3987; A61M 16/0003; A61M 2205/609; A61M 2205/6009

See application file for complete search history.

(56) References Cited

U.S. PATENT DOCUMENTS

| | | | | |
|---|---|---|---|---|
| 6,139,495 | A | * 10/2000 | De La Huerga | A61B 5/411 |
| | | | | 128/903 |
| 6,643,531 | B1 | 11/2003 | Katarow | |
| 6,961,448 | B2 | 11/2005 | Nichols et al. | |
| 7,806,852 | B1 | * 10/2010 | Jurson | A61B 5/1172 |
| | | | | 604/151 |
| 8,753,297 | B2 | 6/2014 | Bystrom et al. | |
| 8,947,848 | B2 | 2/2015 | Musial et al. | |
| 2002/0125991 | A1 | * 9/2002 | Levin | A61B 5/117 |
| | | | | 340/5.8 |
| 2005/0192846 | A1 | * 9/2005 | De Zwart | G06F 19/3418 |
| | | | | 705/3 |
| 2005/0278197 | A1 | 12/2005 | Podczerwinski et al. | |
| 2009/0043180 | A1 | * 2/2009 | Tschautscher | A61B 5/1172 |
| | | | | 600/323 |
| 2009/0138059 | A1 | 5/2009 | Ouwerkerk | |
| 2009/0222539 | A1 | * 9/2009 | Lewis | G06Q 50/24 |
| | | | | 709/221 |
| 2011/0284004 | A1 | * 11/2011 | Silver | A61N 1/3925 |
| | | | | 128/205.13 |
| 2011/0295078 | A1 | 12/2011 | Reid et al. | |
| 2012/0191147 | A1 | * 7/2012 | Rao | A61B 5/1171 |
| | | | | 607/3 |
| 2012/0191476 | A1 | 7/2012 | Reid et al. | |
| 2015/0242812 | A1 | 8/2015 | Nelson et al. | |

FOREIGN PATENT DOCUMENTS

| | | |
|---|---|---|
| KR | 20100051777 A | 5/2010 |
| WO | WO-2008/120154 A2 | 10/2008 |

* cited by examiner

BIOMETRIC IDENTIFICATION IN MEDICAL DEVICES

CROSS-REFERENCE TO RELATED APPLICATIONS

This application claims the benefit of U.S. Provisional Patent Application Ser. No. 62/315,833, filed on Mar. 31, 2016, which is incorporated by reference herein in its entirety for all purposes.

TECHNICAL FIELD

Embodiments of the present disclosure relate generally to electronic devices, and more particularly, to methods and systems for facilitating biometric identification of patients and/or caregivers in medical devices and systems.

BACKGROUND

It is often desirable to be able to identify patients and/or caregivers quickly and efficiently in a medical situation. Known medical devices can use user interfaces that allow patients and/or caregivers to manually enter biographical information, such as name, gender, age, address, and social security number. Alternatively, known medical devices can use scanners to scan a personal identification document associated with a patient and/or a caregiver, such as a driver's license. Such biographical information can then be entered into a patient record for use in identifying the patient.

However, such techniques for identifying patients can fail when the patient cannot communicate with his or her caregivers. For example, if the patient is unconscious, does not speak the same language as his or her caregivers, or is severely mentally or physically impaired, caregivers can be unable to determine the patient's biographical information. In these cases, caregivers can be forced to leave the patient's biographical information blank in the patient's record. The lack of identifying biographical information in the patient's record can lead to errors in matching up the patient's record with other records pertaining to the same patient. In some cases, a patient record can be matched with the wrong patient, or not be matched at all.

Furthermore, known medical devices and techniques for capturing the patient's biographical information, or the caregiver's identity, can be prone to inadvertent mistakes in entering and/or scanning the patient's or caregiver's information. This is especially the case in situations where patient records are updated by caregivers who are pressed for time, as is often the case in emergency situations. These inadvertent mistakes can also lead to errors in matching up the patient's record with other patient records, or with the correct caregiver.

SUMMARY

According to Example 1, the present disclosure is directed to a device for treating a patient, comprising: at least one first sensor configured to measure a physiological parameter of a patient; at least one second sensor configured to detect a characteristic biometric signature associated with the patient; at least one memory; and a control system communicably coupled to the at least one first sensor, the at least one second sensor and the at least one memory, the control system configured to maintain in the at least one memory an emergency encounter record including the at least one physiological parameter of the patient and the characteristic biometric signature.

According to Example 2, the present disclosure is directed to the device of Example 1, wherein the at least one second sensor is configured to detect the characteristic biometric signature at the same time, and/or during the same medical event or medical encounter, as when the at least one first sensor is measuring the physiological parameter of the patient.

According to Example 3, the present disclosure is directed to the device of Examples 1-2, wherein the emergency encounter record is a record of an emergency medical services (EMS) encounter.

According to Example 4, the present disclosure is directed to the device of Example 1-3, wherein the device is configured for use in a mobile emergency response environment.

According to Example 5, the present disclosure is directed to the device of Examples 1-4, further comprising: a data interface configured to receive patient information regarding at least one of a medical condition, a medical history, and biographical information associated with the patient; wherein the emergency encounter record further includes the patient information.

According to Example 6, the present disclosure is directed to the device of any of Examples 1-5, wherein the data interface is a user interface configured to accept user input from a caregiver, the user interface comprising at least one of a physical button, a touchscreen, a microphone, and a video sensor.

According to Example 7, the present disclosure is directed to the device of any of Examples 1-6, wherein the data interface is configured to receive the patient information from a computer-aided dispatch system.

According to Example 8, the present disclosure is directed to the device of any of Examples 1-7, further comprising: a wireless interface configured to communicate with a database at a remote location; wherein the control system is further configured to send the characteristic biometric signature to the database, and to retrieve from the database medical record information associated with the patient.

According to Example 9, the present disclosure is directed to the device of any of Examples 1-8, further comprising: a wireless interface configured to communicate with a database at a remote location; wherein the control system is further configured to send the characteristic biometric signature to the database, and to retrieve from the database biographical information associated with the patient.

According to Example 10, the present disclosure is directed to the device of any of Examples 1-9, further comprising: a data interface configured to communicate with an external computing device; wherein the control system is further configured to upload the emergency encounter record to the external computing device via the data interface.

According to Example 11, the present disclosure is directed to the device of any of Examples 1-10, wherein the emergency encounter record is a first emergency encounter record, and wherein the characteristic biometric signature is a first characteristic biometric signature; and the control system is further configured to determine if the at least one memory is storing a second emergency encounter record including a second characteristic biometric signature that matches the first characteristic biometric signature, and if so, to merge the first emergency encounter record with the second emergency encounter record.

According to Example 12, the present disclosure is directed to the device of any of Examples 1-11, further comprising: a scanner configured to scan a piece of personal identification associated with the patient to determine scanned patient information; wherein the control system is further configured to include the scanned patient information in the emergency encounter record.

According to Example 13, the present disclosure is directed to the device of any of Examples 1-12, wherein the at least one second sensor is a biometric sensor that includes at least one of a fingerprint sensor or scanner, a palm sensor or scanner, an iris sensor or scanner, a retinal sensor or scanner, a facial recognition sensor or scanner, and a voice recognition sensor.

According to Example 14, the present disclosure is directed to the device of any of Examples 1-13, wherein the at least one first sensor is at least one of an electrocardiogram (ECG) sensor, a heartbeat sensor, a blood oxygen sensor, an end-tidal carbon dioxide sensor, and an ultrasound sensor.

According to Example 15, the present disclosure is directed to the device of any of Examples 1-14, wherein the mobile emergency response environment is an ambulance.

According to Example 16, the present disclosure is directed to the device of any of Examples 1-15, wherein the device is the device is selected from the group consisting of, and/or comprising one or more of, a defibrillator configured to deliver a therapeutic electric shock to the patient, an Automated External Defibrillator (AED), a wearable defibrillator, a cardiac monitoring device and a cardiopulmonary resuscitation assistance device.

According to Example 17, the present disclosure is directed to the device of any of Examples 1-16, wherein the at least one first sensor is a blood oxygen sensor configured to fit over a finger of the patient, and wherein the at least one second sensor is a fingerprint scanner disposed on the blood oxygen sensor.

According to Example 18, the present disclosure is directed to the device of any of Examples 1-17, wherein the at least one second sensor is connected to the control system via a wireless connection.

According to Example 19, the present disclosure is directed to the device of any of Examples 1-18, wherein the at least one second sensor is configured to be paired and unpaired to the control system.

According to Example 20, the present disclosure is directed to the device of any of Examples 1-19, wherein the at least one second sensor is part of a smartphone.

According to Example 21, the present disclosure is directed to the device of any of Examples 1-20, wherein the at least one second sensor is configured to be detachable from the control system.

According to Example 22, the present disclosure is directed to the device of any of Examples 1-21, wherein the at least one second sensor is also configured to detect a characteristic biometric signature associated with a caregiver who is treating the patient in the mobile emergency response environment; and the control system is further configured to include the characteristic biometric signature associated with the caregiver in the emergency encounter record.

According to Example 23, the present disclosure is directed to the device of any of Examples 1-22, wherein the at least one first sensor, the at least one second sensor, the at least one memory, and the control system are integrated into a single device.

According to Example 24, the present disclosure is directed to a medical system, the system comprising: at least one first sensor configured to measure a physiological parameter of a patient; at least one second sensor configured to detect a caregiver biometric signature associated with a caregiver; at least one memory; and a control system communicably coupled to the at least one first sensor, the at least one second sensor and the at least one memory, the control system configured to maintain in the at least one memory an emergency encounter record including the at least one measured physiological parameter of the patient and the caregiver biometric signature.

According to Example 25, the present disclosure is directed to the medical system of any of Examples 1-24, wherein the at least one second sensor is configured to detect the caregiver biometric signature at the same time, and/or during the same medical event or medical encounter, as when the at least one first sensor is measuring the physiological parameter of the patient.

According to Example 26, the present disclosure is directed to the medical system of any of Examples 1-25, wherein the medical system is a device selected from the group, and/or comprising one or more of, a defibrillator configured to deliver a therapeutic electric shock to the patient, an Automated External Defibrillator (AED), a wearable defibrillator, a cardiac monitoring device and a cardiopulmonary resuscitation assistance device.

According to Example 27, the present disclosure is directed to the medical system of any of Examples 1-26, wherein the emergency encounter record is a record of an emergency medical services (EMS) encounter.

According to Example 28, the present disclosure is directed to the medical system of any of Examples 1-27, wherein the medical system is configured for use in a mobile emergency response environment.

According to Example 29, the present disclosure is directed to the medical system of any of Examples 1-28, the system further comprising: a data interface configured to receive patient information regarding at least one of a medical condition, a medical history, and biographical information associated with the patient; wherein the emergency encounter record further includes the patient information.

According to Example 30, the present disclosure is directed to the medical system of any of Examples 1-29, wherein the data interface is a user interface configured to accept user input from a caregiver, the user interface comprising at least one of a physical button, a touchscreen, a microphone, and a video sensor.

According to Example 31, the present disclosure is directed to the medical system of any of Examples 1-30, wherein the data interface is configured to receive the patient information from a computer-aided dispatch system.

According to Example 32, the present disclosure is directed to the medical system of any of Examples 1-31, wherein the caregiver is a first caregiver and the caregiver biometric signature is a first caregiver biometric signature, the at least one second sensor is further configured to measure a second caregiver biometric signature associated with a second caregiver; and the emergency encounter record further includes the second caregiver biometric signature.

According to Example 33, the present disclosure is directed to the medical system of any of Examples 1-32, the system further comprising: a user interface configured to accept user input indicating a medical event; wherein the emergency encounter record further includes a record of the medical event and an association between the medical event and the caregiver biometric signature.

According to Example 34, the present disclosure is directed to the medical system of any of Examples 1-33, wherein the record of the medical event includes a record of the at least one measured physiological parameter before the medical event, and a record of the at least one measured physiological parameter after the medical event.

According to Example 35, the present disclosure is directed to the medical system of any of Examples 1-34, wherein the caregiver is a first caregiver and the caregiver biometric signature is a first caregiver biometric signature; the at least one second sensor is further configured to measure a second caregiver biometric signature associated with a second caregiver; the medical event is a first medical event; the user interface is further configured to accept user input indicating a second medical event; and the emergency encounter record further includes a record of the second medical event and an association between the second medical event and the second caregiver biometric signature.

According to Example 36, the present disclosure is directed to the medical system of any of Examples 1-35, wherein the user interface comprises the at least one second sensor, the at least one second sensor configured to cause the control system to store the record of the medical event and the association in the emergency encounter record when the at least one second sensor detects the caregiver biometric signature.

According to Example 37, the present disclosure is directed to the medical system of any of Examples 1-36, wherein the medical event comprises at least one of an administration of medication, an administration of a defibrillating electric shock, an administration of a pacing electric shock, an administration of cardiopulmonary resuscitation (CPR), transmission of an electrocardiogram (ECG) trace to a remote facility, and an endotracheal intubation.

According to Example 38, the present disclosure is directed to a server for maintaining patient records including biometric data associated with caregivers, the server comprising: at least one memory storing a plurality of patient records, each patient record being associated with a corresponding patient, each patient record comprising (i) patient information regarding at least one of a medical condition, a medical history, and biographical information associated with the corresponding patient, and (ii) a caregiver biometric signature associated with a caregiver of the corresponding patient; a data interface; and at least one processor configured to: receive, via the data interface, a request for a patient record of the plurality of patient records, and send, in response to the request, via the data interface, the requested patient record.

According to Example 39, the present disclosure is directed to the medical system and/or server of any of Examples 1-38, wherein at least some of the patient records further comprise at least one measured physiological parameter of the corresponding patient.

According to Example 40, the present disclosure is directed to the medical system and/or server of any of Examples 1-39, wherein the caregiver is a first caregiver and the caregiver biometric signature is a first stored caregiver biometric signature; and at least some of the patient records further comprise a second caregiver biometric signature associated with a second caregiver of the corresponding patient.

According to Example 41, the present disclosure is directed to the medical system and/or server of any of Examples 1-40, wherein at least some of the patient records further comprise at least one association of the caregiver biometric signature with a record of a medical event.

According to Example 42, the present disclosure is directed to the medical system and/or server of any of Examples 1-41, wherein at least some of the patient records further comprise at least one association of the first caregiver biometric signature with a first set of one or more records of medical events, and at least one association of the second caregiver biometric signature with a second set of one or more records of medical events.

According to Example 43, the present disclosure is directed to the medical system and/or server of any of Examples 1-42, wherein the record of the medical event includes a record of at least one measured physiological parameter before the medical event and a record of the at least one measured physiological parameter after the medical event.

According to Example 44, the present disclosure is directed to the medical system and/or server of any of Examples 1-43, wherein the medical event comprises at least one of an administration of medication, an administration of a defibrillating electric shock, an administration of a pacing electric shock, an administration of cardiopulmonary resuscitation (CPR), transmission of an electrocardiogram (ECG) trace to a remote facility, and an endotracheal intubation.

According to Example 45, the present disclosure is directed to the medical system and/or server of any of Examples 1-44, wherein the at least one processor is further configured to: receive, via the data interface, a request for patient records associated with a specific caregiver; determine a specific biometric signature associated with the specific caregiver; determine which patient records of the plurality of patient records comprise a caregiver biometric signature that matches the specific biometric signature; and returning, via the data interface, a list of the patient records which comprise a caregiver biometric signature that matches the specific biometric signature.

Figure 1:
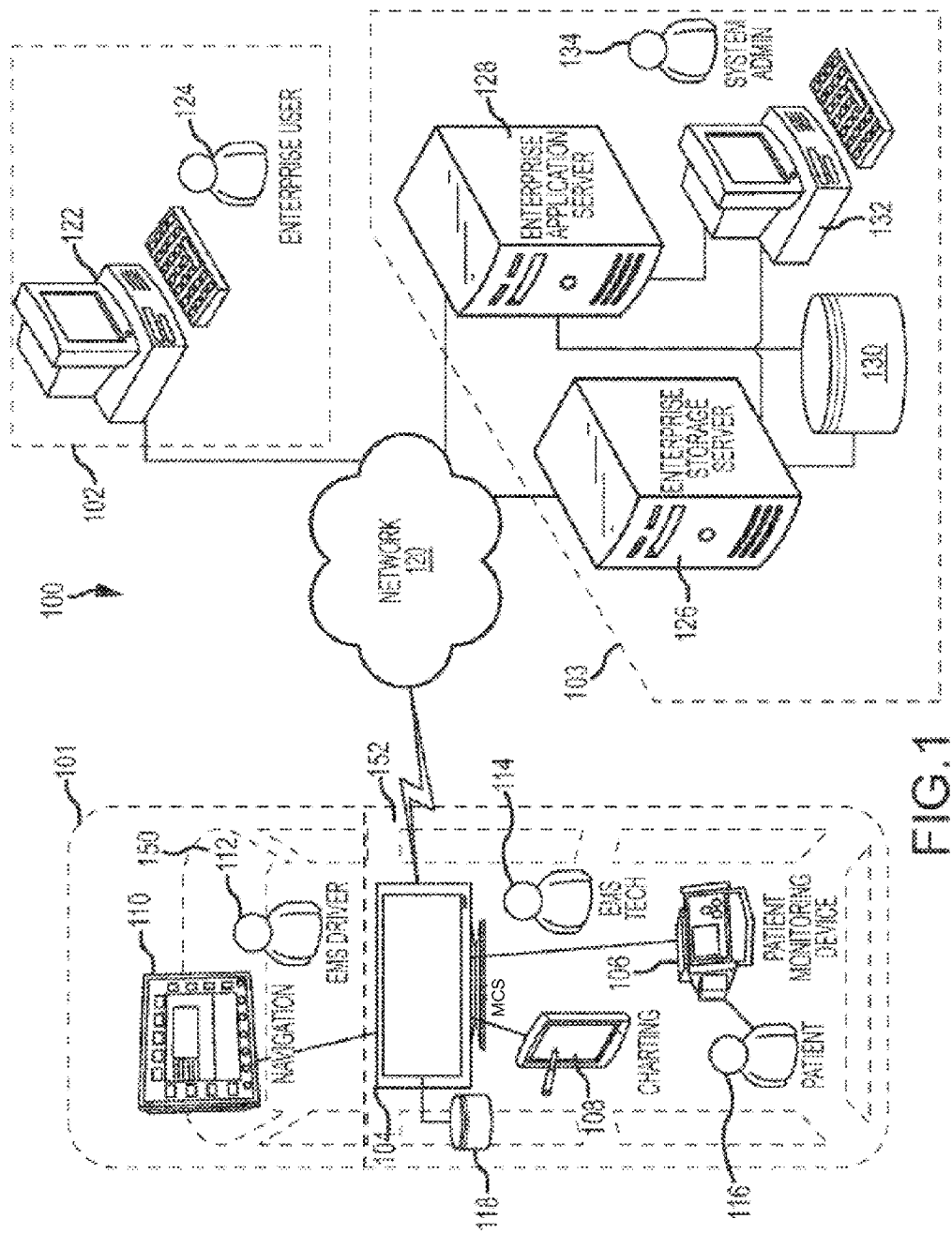
FIG. 1 illustrates a system for mobile and enterprise real-time display of medical information collected from multiple different EMS devices, according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Medical devices or systems are often used in situations where it is desirable to quickly and reliably identify a patient and/or a caregiver in a patient's record. Even if the patient or caregiver cannot be affirmatively identified when the patient's record is being updated, it can be desirable to embed one or more uniquely identifiable pieces of information regarding the patient and/or the caregiver in the patient's medical record. These uniquely identifiable pieces of information can then be used to facilitate identifying the patient and/or the caregiver at a later time.

For example, consider the illustrative scenario of a crew of emergency medical services (EMS) caregivers in an ambulance being called upon to pick up and treat a patient suffering from an emergency medical condition (e.g., a heart attack, or a traumatic injury), and to deliver the patient to a treating hospital. During the course of the emergency encounter, the EMS caregivers can create a patient record. As used herein, a patient record can be a record of information that relates to a patient. In some embodiments, the patient record can be or can include an emergency encounter record. As used herein, an emergency encounter record can comprise a patient record that relates to an emergency encounter. An emergency encounter record can also comprise a record of an emergency medical services (EMS) encounter that captures the actions and observations of one or more EMS caregivers during the course of an EMS call relating to a patient. This record of actions and observations can include physiological parameters of the patient recorded during the course of the EMS encounter. For example, an emergency encounter record that relates to an EMS encounter can include a record of actions and/or observations starting from when EMS caregivers are tasked with responding to a specific EMS call (e.g., when an ambulance crew is directed to respond to an emergency medical call), through the time when EMS caregivers pick up and treat a patient, until the time when EMS caregivers conclude their care for the patient, such as when the EMS caregivers hand off the patient to other healthcare providers (e.g., when the patient is delivered to a hospital) or when the EMS caregivers determine that no further patient care is needed. An emergency encounter record can also comprise a record of an EMS encounter relating to multiple EMS calls relating to the same patient. An emergency encounter record can comprise a record of observed patient symptoms during the encounter, observed patient physiological parameters (such as heart rate, ECG traces, temperature, blood-oxygen data, and the like), and treatments or medications administered during the encounter. The emergency encounter record can also include information that the patient communicates to the EMS caregivers, such as any known allergies to medication, relevant medical history, and/or additional patient symptoms. As will be discussed in further detail below, each emergency encounter record can also include one or more biometric signatures associated with one or more patients, as well as one or more biometric signatures associated with one or more caregivers.

Patient records, which include but are not limited to emergency encounter records, can generally include biographical information regarding the patient, such as the patient's name, address, age, and social security number. This biographical information can be used to later identify the patient and/or to match the patient record with other medical records pertaining to the patient. However, EMS caregivers or other healthcare providers can sometimes be confronted with a patient who is unconscious, too mentally or physically impaired to communicate, or who does not speak the same language as the caregivers. The EMS caregivers and/or other healthcare providers can also be unable to locate any personally identifying document on the patient's person. In these cases, healthcare providers can be forced to omit some or all of the personally identifiable biographical information regarding the patient that they would normally collect (e.g., the patient's name, age, address, and social security number). In the case of EMS caregivers, when the EMS caregivers deliver the patient to the treating hospital, the hospital can identify the patient through other means. However, since the patient record generated by the EMS caregivers during the emergency encounter did not include any uniquely identifiable information regarding the patient, hospital staff can have difficulty matching the patient record with subsequently generated hospital records pertaining to the same patient. In some cases, the patient's record can be incorrectly paired with the wrong patient, and/or the patient's record can be lost.

It can also be desirable to include information in the patient record that identifies the caregiver, or caregivers, who treated the patient. This information can indicate a single caregiver who treated the patient and/or had primary responsibility for the patient's care, multiple caregivers who treated the patient, and/or all caregivers who treated the patient at any point during a period of time, such as an emergency encounter. This information can also indicate which caregivers were associated with particular medical events in the patient record. For example, this information can indicate which caregiver administered a certain medication, delivered a defibrillator shock at a certain time, took a reading of a particular physiological parameter at a particular time, or performed CPR on the patient. This information can be used to ensure compliance. For instance, certain rules and/or regulations may require that certain treatments or medications, such as delivery of defibrillator shocks, be administered only by caregivers who are sufficiently qualified, such as paramedics (instead of basic emergency medical technicians). Information regarding which caregivers administered which treatments can be audited to ensure compliance with such rules and/or regulations. Furthermore, high-performing or under-performing caregivers can also be identified based on audits of patient records and analysis of patient outcomes. Correlations in patient outcomes with caregiver characteristics, such as age, experience, or training, can also be identified by analyzing a population of patient records.

Some embodiments of the present disclosure include systems, apparatus, and methods for collecting one or more uniquely identifiable biometric signatures from a patient. In some cases, these biometric signature(s) (also referred to as biometric data herein) can be collected during the course of an emergency encounter; in other cases, these biometric signatures can be collected in a non-emergency setting. As used herein, biometric signatures can be any piece of biometric data pertaining to, noting, and/or using a person's unique physical and/or other traits for the purposes of identification. Biometric signatures can include one or more of, and/or one or a combination of, fingerprints, palm prints, iris scans, retinal scans, facial recognition scans, voice/voiceprint recognition or identification data and/or other biological traits or characteristics that may be unique to the patient or otherwise used to identify the patient or that are associated with the patient, and can be collected using a sensor, e.g., a biometric sensor, that is associated with and/or integrated into a medical device. Exemplary biometric sensors include but are not limited to: a fingerprint sensor, a palm sensor, an iris sensor, a retinal sensor, a facial recognition sensor and voice recognition sensor. In certain embodiments, a combination of two or more of any of the above mentioned biometric signatures can be collected, e.g., during the course of an emergency encounter or in a non-emergency setting, to ensure the accuracy of the patient identification. The medical device, for example, can be an emergency medical device used by EMS caregivers during the course of an emergency encounter. The medical device can also perform other functions, such as monitor patient vital signs, receive and record notes and textual information, communicate with other devices via a short-range wireless or wired connection (e.g., other devices within an ambulance) or a long-range wireless connection (e.g., via a cellular wireless link with a device at a hospital or other facility), and/or deliver a therapeutic treatment (e.g., administering drugs or delivering therapeutic electric shocks). The medical device can also be configured to record and/or maintain a patient record, and to embed the patient biometric data into the patient record for use in later confirming and/or determining an identity of the patient, and/or for matching the patient record with other patient records.

Other embodiments of the present disclosure include systems, apparatus, and methods for collecting one or more uniquely identifiable biometric signatures from one or more caregivers. These caregiver biometric signatures (also referred to as caregiver biometric data herein) can be captured during the course of an emergency encounter; in other cases, these caregiver biometric signature(s) can also be captured in non-emergency settings. Caregiver biometric signatures can be the same as or similar to patient biometric signatures described above, and can also include one or more of, and/or one or a combination of, fingerprints, palm prints, iris scans, retinal scans, facial recognition scans, voice/voiceprint recognition or identification data and/or other biological traits or characteristics that may be unique to the caregiver or otherwise used to identify the caregiver or that are associated with the caregiver. Caregiver biometric signatures can also be collected by a sensor, e.g., a biometric sensor, that is associated with and/or integrated into a medical device. Exemplary biometric sensors include but are not limited to: a fingerprint sensor, a palm sensor, an iris sensor, a retinal sensor, a facial recognition sensor and voice recognition sensor. In certain embodiments, a combination of two or more of any of the above mentioned biometric signatures can be collected, e.g., during the course of an emergency encounter or in a non-emergency setting, to ensure the accuracy of the caregiver identification. In some embodiments, the medical device can be an emergency medical device used by EMS caregivers during the course of an emergency encounter. The medical device can also be configured to embed the caregiver biometric data into the patient record. This caregiver biometric data can be used to confirm and/or identify one or more caregivers in a patient record. In certain embodiments, the caregiver's biometric signature/data may be required to gain access to a device to reconfigure or modify the device. For example, a supervisor may be required to provide their fingerprint in order to obtain access to a device or to access a supervisor or owner menu to change device configurations or to update software on the device. The supervisor's biometric signature/data may be used to authenticate the supervisor's identity and allow the supervisor to change or update configurations, software or other features on the device.

Yet other embodiments of the present disclosure include systems, apparatus, and methods for receiving patient biometric and/or caregiver biometric data or signatures, and to determine if the received biometric data or signature corresponds to one or more records regarding a patient and/or a caregiver. If the received biometric data does correspond to one or more such records, the matched records can be returned. Multiple different techniques for matching received biometric data with stored biometric data can be used for determining if the received biometric data corresponds to one or more patient and/or caregiver records. These techniques can include, without limitation, image-based techniques, pattern-based techniques, correlation-based techniques, minutia-based techniques, and non-minutia-based techniques. These techniques can match part of a biometric signature, (e.g., part of a patient's finger or palm print), or can match complete biometric signatures. In certain embodiments, the biometric data or signatures may be used to detect mismatches and potential discontinuities in data records to mitigate or prevent user error, and to help create accurate patient medical records. For example, using a patient's biometric signature, associated with collected patient data, to locate the patient's medical record, e.g., in the cloud or another database, helps ensure that the collected data will be added to or matched with the correct patient record for that particular patient.

In certain embodiments, a patient's biometric data or signature may be used to accurately locate or identify the patient's biographical data and/or medical records/history. For example, a patient's biometric data or signature may be used to identify or locate that patient's medical record, so that the caregiver can use the patient's medical information to guide the patient's therapy. Once located or identified, the record may be downloaded, e.g., from the cloud or another database, to a local device or server, or otherwise accessed. The caregiver can access the patient's medical record and use information from the patient's medical record, e.g., known allergies, medications taken, and other patient data, to provide the patient with the best and safest treatment and improve the level of care given to the patient. The patient's medical information may help in the decision-making process to properly treat the patient, and help guide the patient's therapy.

As illustrated in FIG. 1, a system 100 according to embodiments of the present disclosure performs advanced data management, integration and presentation of EMS data from multiple different devices. System 100 includes a mobile environment 101, an enterprise environment 102, and an administration environment 103. Devices within the various environments 101, 102, 103 may be communicably coupled via a network 120, such as, for example, the Internet.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

According to embodiments of the present disclosure, the mobile environment 101 is an ambulance or other EMS vehicle-for example a vehicular mobile environment (VME). The mobile environment may also be the local network of data entry devices as well as diagnostic and therapeutic devices established at time of treatment of a patient or patients in the field environment, such as an "At Scene Patient Mobile Environment" (ASPME). The mobile environment may also be a combination of one or more of VMEs and/or ASPMEs. The mobile environment may include a navigation device 110 used by the driver 112 to track the mobile environment's position 101, locate the mobile environment 101 and/or the emergency location, and locate the transport destination, according to embodiments of the present disclosure. The navigation device 110 may include a Global Positioning System ("GPS"), for example. The navigation device 110 may also be configured to perform calculations about vehicle speed, the travel time between locations, and estimated times of arrival. According to embodiments of the present disclosure, the navigation device 110 is located at the front of the ambulance to assist the driver 112 in navigating the vehicle. The navigation device 110 may be, for example, a RescueNet® Navigator onboard electronic data communication system available from Zoll Data Systems of Broomfield, Colo.

As illustrated in FIG. 1, a patient monitoring device 106 and a patient charting device 108 are also often used for patient care in the mobile environment 101, according to embodiments of the present disclosure. The EMS technician 114 attaches the patient monitoring device 106 to the patient 116 to monitor the patient 116. The patient monitoring device 106 may be, for example, a defibrillator device with electrodes and/or sensors configured for attachment to the patient 116 to monitor heart rate and/or to generate electrocardiographs ("ECG's"), for example a portable defibrillator and/or monitor and/or an automated external defibrillator (AED), and/or a wearable medical device or wearable defibrillator, according to embodiments of the present disclosure. The patient monitoring device 106 may be, for example, a ventilator. The patient monitoring device 106 may also include sensors to detect or a processor to derive or calculate other patient conditions. For example, the patient monitoring device 106 may monitor, detect, treat and/or derive or calculate blood pressure, temperature, respiration rate, blood oxygen level, end-tidal carbon dioxide level, pulmonary function, blood glucose level, and/or weight, according to embodiments of the present disclosure. The patient monitoring device 106 may be a ZOLL E-Series®, X-Series®, R-Series®, Lifevest® wearable defibrillator or other defibrillator or a ZOLL ventilator, available from ZOLL Medical Corporation of Chelmsford, Mass., according to embodiments of the present disclosure. A patient monitoring device may also be a patient treatment device, or another kind of device that includes patient monitoring and/or patient treatment capabilities, according to embodiments of the present disclosure. For example, if the patient monitoring device is a defibrillator, the patient monitoring device can also deliver therapeutic electric shocks to the patient. In other embodiments, the patient monitoring device can also deliver other types of treatments, such as operating a respirator, or administering drugs or other medication. As used herein, a device for treating a patient includes a patient treatment device, a monitoring device, and/or a device that treats and monitors a patient. A patient monitoring and/or a patient treatment device may be utilized in accordance with certain embodiments described herein.

In some embodiments, the patient monitoring device 106 may be configured for monitoring one or more physiological parameters of the patient. For example, such a patient monitoring device can include a cardiac monitoring device or a cardiac monitor that is configured to monitor one or more cardiac parameters of the patient, e.g., for remotely monitoring and/or diagnosing a cardiac condition of the patient. For example, such cardiac parameters may include a patient's electrocardiogram (ECG) information, including heart rate information, heart sounds (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., continuous or substantially continuous monitoring for 7 days, 15 days, 30 days, or more as appropriate.

In mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others.

The patient charting device 108 can be a device used by the EMS technician 114 to generate records and/or notes about the patient's 116 condition and/or treatments applied to the patient, according to embodiments of the present disclosure. For example, the patient charting device 108 may be used to note a dosage of medicine given to the patient 116 at a particular time. The patient charting device 108 and/or patient monitoring device 106 may have a clock, which may be synchronized with an external time source such as a network or a satellite to prevent the EMS technician from having to manually enter a time of treatment or observation (or having to attempt to estimate the time of treatment for charting purposes long after the treatment was administered), according to embodiments of the present disclosure. The patient charting device 108 may also be used to record biographic and/or demographic and/or historical information about a patient, for example the patient's name, identification number, height, weight, and/or medical history, according to embodiments of the present disclosure. According to embodiments of the present disclosure, the patient charting device 108 is a tablet PC, such as for example the TabletPCR component of the RescueNet® ePCR Suite available from ZOLL Data Systems of Broomfield, Colo. According to some embodiments of the present disclosure, the patient charting device 108 is a wristband or smart phone such as an Apple iPhone or iPad with interactive data entry interface such as a touch screen or voice recognition data entry that may be communicably connected to the MCS device 104 and tapped to indicate what was done with the patient 116 and when it was done. According to some embodiments of the present disclosure, the patient charting device 108 can be integrated with the patient monitoring device 106, such that a single device can be configured to monitor the patient, treat the patient, as well as to generate records and/or notes about the patient's 116 condition and/or treatments applied to the patient.

The navigation device 110, the charting device 108, and the monitoring device 106 are each separately very useful to the EMS drivers 112 and technicians 114 before, during, and after the patient transport. A "mobile computing system" ("MCS") device 104 receives, organizes, stores, shares, distributes, and displays data from each device 108, 110, 112 to further enhance the usefulness of each device 108, 110, 112 and to make it much easier for the EMS technician 114 to perform certain tasks that would normally require the EMS technician 114 to divert visual and manual attention to each device 108, 110, 112 separately, according to embodiments of the present disclosure. In other words, the MCS device centralizes, organizes, and shares information that would normally be de-centralized and disorganized, according to embodiments of the present disclosure.

Although device 104 is referred to herein as a "mobile computing system" device because the EMS technician 114 would normally benefit the most from having such a display device mounted in the back 152 of an ambulance or vehicle or other mobile operation, one of ordinary skill in the art, based on the disclosure provided herein, will recognize that some or all of the MCS device 104 may be located in any part of a mobile environment 101, EMS vehicle, and/or anywhere else useful to an EMS technician 114. For example, the MCS device 104 may be located in the front 150 of an ambulance, and/or may include components that are portable and can be carried into a patient residence, according to embodiments of the present disclosure.

The MCS device 104 is communicably coupled to the patient monitoring device 106, the patient charting device 108, and the navigation device 110, according to embodiments of the present disclosure. The MCS device 104 is also communicably coupled to a storage medium 118. The MCS device 104 may be a touch-screen, flat panel PC, and the storage medium 118 may be located within or external to the MCS device 104, according to embodiments of the present disclosure. The MCS device 104 may include a display template serving as a graphical user interface, which permits the user (e.g. EMS tech 114) to select different subsets and/or display modes of the information gathered from and/or sent to devices 106, 108, 110, according to embodiments of the present disclosure.

According to embodiments of the present disclosure, the MCS device 104 not only seamlessly integrates information from a patient monitoring device 106, a patient charting device 108, and a navigation device 110 for display in mobile environment 101, but it also does so for display in a remote environment such as, for example, enterprise environment 102. Enterprise environment 102 may be a hospital and/or dispatch environment, for example.

Data from the MCS device 104 (and therefore data from the devices 106, 108, 110 communicably coupled with the MCS device 104) may be received by one or more enterprise storage servers 126 in an administration environment 103 and stored in an enterprise database 130, and the same information may be accessed and provided by one or more enterprise application servers 128 to a workstation 122 of an enterprise user 124, according to embodiments of the present disclosure. According to embodiments of the present disclosure, the MCS device 104 is communicably coupled to the storage server 126 which is communicably coupled to the database 130, and the application server 128 is communicably coupled to the database and to the enterprise workstation 122. Such devices may be communicably coupled via a network 120 such as, for example, the Internet.

When the MCS device 104 receives updated information from one or more of the devices (e.g. devices 106, 108, 110) to which it is communicably coupled, the MCS device 104 sends the updated information to the enterprise storage server 126, which stores the updated information in a database which may be contained on a storage medium 130, according to embodiments of the present disclosure. Hence, information from one or more devices (e.g. devices 106, 108, 110) may be stored in mobile database 118, remote enterprise database 130, or both, according to embodiments of the present disclosure. An enterprise user 124, who may be an emergency room nurse monitoring and/or preparing for ambulance arrivals, an emergency room physician, and/or a medical director at home, for example, may access information similar to information displayed by the MCS device 104 by requesting the information via an enterprise workstation 122. For example, the enterprise workstation 122 accesses a web interface and/or thin client web browser application which requests the information over the network 120 from application server 128. Application server 128 queries the database 130 for the information, and returns a display to enterprise workstation 122 that looks the same as or similar to what the EMS technician 114 is currently seeing on the MCS device 104 display, according to embodiments of the present disclosure.

MCS device 104 can also share information with one or more of the devices (e.g., devices 106, 108, 110). For example, information generated from one of the devices 106, 108, and/or 110 can be collected and then shared with one or more of the other devices. MCS device 104 can also receive information from enterprise application server 128, and/or enterprise storage server 126, and either display such information itself, or share such information with devices 106, 108, and/or 110. For example, if patient monitoring device 106 takes an ECG reading of a patient, or if the patient monitoring device 106 administers a treatment (such as medication or a defibrillation shock), the ECG reading and/or treatment can be shared, via MCS device 104 or directly, with patient charting device 108 for storage in a patient record maintained therein. In another example, MCS device 104 can be configured to receive patient information, such as medical records, known medical conditions, and biographical information, and to share this information with devices 106, 108, and/or 110. This biographical information can be inserted into a patient record being maintained in patient charting device 108. A biometric sensor associated with any of the devices depicted in FIG. 1, including devices 106, 108, 110, and/or 104, can also be configured to take and record a biometric signature associated with a patient and/or a caregiver, and to insert this biometric signature into the patient record being maintained in patient charting device 108. Alternatively, this biographical information can inform a treatment being administered by patient monitoring device 106, and/or navigation data displayed by navigation device 110.

Although FIG. 1 depicts a single MCS device 104 in the mobile environment 101, more than one MCS device 104 may be used in the mobile environment 101 to communicably connect to the same or a different set of devices 106, 108, 110. And although FIG. 1 depicts one mobile environment 101, more than one mobile environment 101 and/or more than one MCS device 104 may be communicably coupled with the administration environment 103 and/or the enterprise storage server 126, according to embodiments of the present disclosure. According to embodiments of the present disclosure, the enterprise storage server 126 receives EMS device information from MCS device 104 and stores it in database 130 along with an authenticated time stamp and an identifier associating the information with a particular EMS device and/or a particular EMS vehicle. In this way, data from multiple vehicles and/or multiple devices may be accessed by the enterprise user 124.

Also, the enterprise storage server 130 may securely store the information received from one or more MCS devices 104 for longer periods of time to permit later use of the information. For example, the MCS device 104 may receive patient-identifying information such as name, address, and/or social security number via the patient charting device 108 or directly through the MCS device 104, and then may convey some or all of the patient-identifying information to enterprise storage server 126 with a request for the enterprise storage server 126 to query the database 130 for past records involving the same patient 116. The MCS device 104 may also include a biometric signature associated with a patient in place of, or as part of, the patient-identifying information to enterprise storage server 126. The enterprise storage server 126 can use the patient-identifying information and/or the patient biometric signature to search for and identify past records involving the same patient. When using a patient's biometric signature to search for/identify past records, enterprise storage server 126 can use a variety of techniques to match a patient's biometric signature received from MCS device 104 with recorded biometric signatures. As discussed above, these techniques can include, without limitation, image-based techniques, pattern-based techniques, correlation-based techniques, minutia-based techniques, and non-minutia-based techniques. These techniques can match part of a biometric signature, (e.g., part of a patient's finger or palm print), or can match complete biometric signatures.

The enterprise storage server 126 may then forward any such records or portions of such records back to the MCS device 104 (e.g. for display in the patient charting screen or the Past Medical History in the patch notes screen) to assist the EMS technician 114 with the current emergency. Similarly, such past EMS encounter record information may also be accessed by the enterprise user 124, according to embodiments of the present disclosure. A system administrator 134 may access and/or monitor the data in database 130 and/or modify the instructions of the servers 126, 128 via administration workstation 132, which may be communicably coupled to the servers 126, 128, according to embodiments of the present disclosure.

According to some embodiments of the present disclosure, the MCS device 104 may connect with (e.g. automatically or manually or selectively) a wearable medical device, such as, for example, a Lifevest® wearable defibrillator, to receive and display patient monitoring information therefrom. The MCS device 104 may also be configured to receive patient-identifying information from such a wearable device, to permit the MCS device 104 to query an external database, for example across network 120, to retrieve additional information about the patient. The MCS device 104 may also be configured to connect with an implantable cardioverter-defibrillator ("ICD") in a similar fashion, according to embodiments of the present disclosure.

Further details regarding system 100 can be found in US Patent Application Publication No. 2011/0172550, titled "SYSTEMS AND METHODS FOR EMS DEVICE COMMUNICATION INTERFACE," published Jul. 14, 2011, the entire contents of which are incorporated herein by reference.

Figure 2:
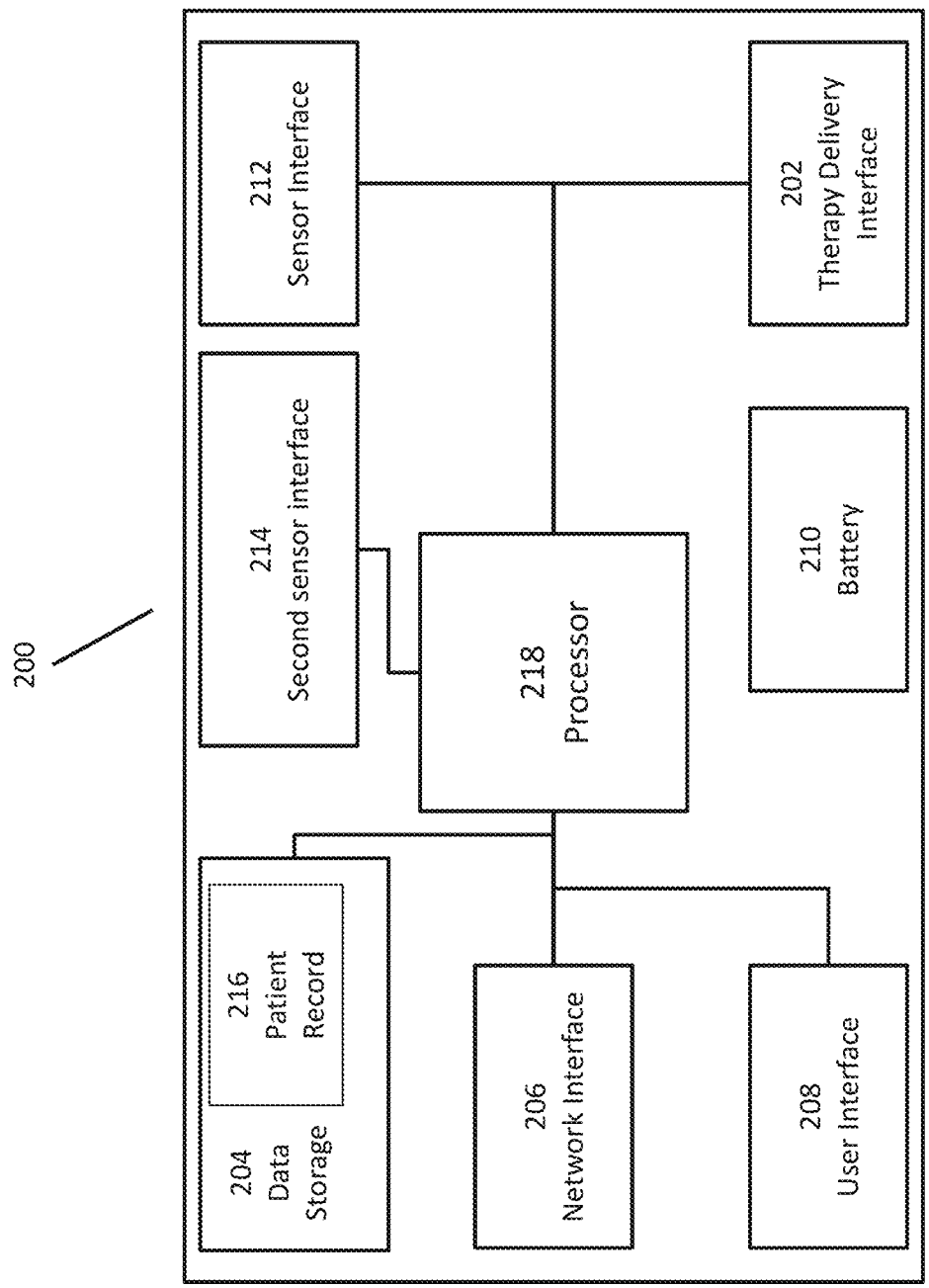
FIG. 2 illustrates a medical device controller, according to some embodiments.

FIG. 2 illustrates a medical device controller 200 that is configured to monitor a patient, monitor the patient's environment, or administer a treatment to a patient. Some or all of the illustrated components of the medical device controller 200 may, for example, be configured for use in a patient monitoring device 106, a patient charting device 108, a MCS device 104, or may be dispersed across two or more of these devices, as well as other devices. At a high level, medical device controller 200 can be configured to facilitate monitoring a patient's physiological parameters (e.g., ECG trace, heart rate, temperature), record information about the patient's 116 condition, treatments applied to the patient, and/or biographical information about the patient into a patient record, and to embed one or more characteristic biometric signatures associated with the patient and/or a caregiver into the patient record and/or another record.

As shown in FIG. 2, the medical device controller 200 can include a sensor interface 212, a therapy delivery interface 202, a battery 210, a user interface 208, a network interface 206, a data storage 204 storing a patient record 216, a second sensor interface 214, and a processor 218. Medical device controller 200 can also be modified to omit any of the above components, or to include additional components.

In this illustrated example, the battery 210 is a rechargeable 3 cell 2200 mAh lithium ion battery pack that can provide electrical power to the other device components with a minimum 24 hour run time between charges. The battery capacity, runtime, and type (e.g., lithium ion, nickel-cadmium, or nickel-metal hydride) can be changed to best fit the specific application of the medical device controller 100. Although FIG. 2 does not illustrate a connection between battery 210 and any other component, the battery 210 provides power to some or all of the components in FIG. 2, according to an embodiment of the present disclosure.

According to the embodiment illustrated in FIG. 2, the processor 218 is communicably coupled to a plurality of peripheral devices, including the sensor interface 212, the therapy delivery interface 202, the user interface 208, the network interface 206, the data storage 204 storing a patient record 216, and/or the second sensor interface 214. Some or all of the peripheral devices disclosed in FIG. 2 can be connected directly with the processor 218, or can be indirectly connected via intermediate components (not shown) such as analog-to-digital converters, serial-to-parallel converters, data buses, wired or wireless interfaces (e.g., components may not be integrated into the same device), buffers and/or amplifiers. The processor 218 can perform a series of instructions that result in manipulated data which are stored in and retrieved from the data storage 204. According to a variety of embodiments, the processor 218 can be a commercially available processor such as a processor manufactured by Texas Instruments, Intel, AMD, Sun, IBM, Motorola, Freescale, and ARM Holdings. However, the processor 218 may be any type of processor, multi-processor or controller, whether commercially available or specially manufactured. For instance, according to one embodiment, the processor 218 may include a power conserving processor arrangement such as described in issued U.S. Pat. No. 8,904,214, titled "SYSTEM AND METHOD FOR CON- SERVING POWER IN A MEDICAL DEVICE," filed Jul. 9, 2010 (hereinafter the "'096 application"), which is hereby incorporated herein by reference in its entirety. In another embodiment, the processor 118 is an Intel® PXA270.

In some embodiments, the processor 218 can comprise two or more processors or two or more processor cores. In some cases, at least some of these processors or processor cores can be configured to execute a conventional real-time operating system (RTOS), such as RTLinux. At least some of these processors or processor cores can also be configured to execute a conventional general-purpose operating system (GPOS), such as BSD or BNU/Linux. In these embodiments, the RTOS may provide platform services to application software, such as some embodiments of the second sensor interface 214 or the therapy delivery interface 202, or applications being executed on one or more processors or processor cores implementing a GPOS. These platform services may include inter-process and network communication, file system management and standard database manipulation. One or more of many operating systems may be used, and embodiments are not limited to any particular operating system or operating system characteristic.

Data storage 204 can include both volatile data storage and/or non-volatile data storage configured to store non-transitory instructions and/or data. Non-volatile data storage can include any device for storing non-volatile data with sufficient throughput and storage capacity to support the functions described herein. Volatile memory can be any type of volatile memory that supports the operations of processor 218 during execution of its instructions. In some embodiments, the processor memory includes a relatively high performance, volatile, random access memory such as dynamic random access memory (DRAM), static memory (SRAM) or synchronous DRAM. Data storage 204 can include patient record 216 (either in volatile or non-volatile data storage), which is described in greater detail below.

A variety of components can manage data movement between data storage 204 and processor 218, and embodiments are not limited to particular data management components. Further, embodiments are not limited to a particular memory, memory system or data storage system. The instructions stored on the data storage 204 can include executable programs or other code that can be executed by the processor 218. The instructions may be persistently stored as encoded signals, and the instructions may cause the processor 218 to perform the functions described herein. Data storage 204 also can include information that is recorded, on or in, the medium, and this information may be processed by the processor 218 during execution of instructions. The medium can, for example, be optical disk, magnetic disk or flash memory, among others, and can be permanently affixed to, or removable from, the medical device controller 200.

As shown in FIG. 2, the medical device controller 200 can also optionally include several system interface components, such as sensor interface 212, therapy delivery interface 202, user interface 208, network interface 206, and/or second sensor interface 214. Each of these system interface components can be configured to exchange, i.e., send or receive, data with one or more specialized devices that can be located within the housing of the medical device controller 200 or elsewhere. The components used by the interfaces 212, 202, 206, 208, and/or 214 can include hardware components, software components, or a combination of both. Within each interface, these components physically and logically couple the medical device controller 200 to the specialized devices. This physical and logical coupling enables the medical device controller 200 to both communicate with and, in some instances, power or control the operation of the specialized devices. These specialized devices can include physiological sensors; therapy delivery devices; computer networking devices; user interfaces such as displays, keyboards, trackpads, and touchscreens; and biometric sensors.

According to various embodiments, the hardware and software components of the interfaces 212, 202, 206, 208, and 214 implement a variety of coupling and communication techniques. In some embodiments, the interfaces 212, 202, 206, 208, and/or 214 use leads, cables or other wired connectors as conduits to exchange data between the medical device controller 200 and specialized devices. In other embodiments, the interfaces 212, 202, 206, and 214 communicate with specialized devices using wireless technologies such as radio frequency, Bluetooth, WiFi, or infrared technology. The software components included in the interfaces 212, 202, 206, 208, and 214 enable the processor 218 to communicate with specialized devices. These software components can include elements such as objects, executable code, and populated data structures. Together, these software components provide software interfaces through which the processor 218 can exchange information with specialized devices. Moreover, in at least some embodiments according to which one or more specialized devices communicate using analog signals, the interfaces 212, 202, 206, 208, and 214 further include components configured to convert analog information into digital information, and vice versa, to enable the processor 218 to communicate with specialized devices.

As discussed above, the system interface components 212, 202, 206, 208, and 214 shown in the embodiment of FIG. 2 support different types of specialized devices. For instance, the components of the sensor interface 212 can couple the processor 218 to one or more physiological sensors such as body temperature sensors, respiration monitors, electrocardiogram (ECG) sensing electrodes, blood oxygen sensors, blood pressure sensors and heart rate sensors, and/or one or more environmental sensors such as atmospheric thermometers, airflow sensors, video sensors, audio sensors, accelerometers, GPS locators, and hygrometers. In these embodiments, the sensor may include sensors with a relatively low sampling rate, such as wireless sensors.

The components of the therapy delivery interface 202 can couple one or more therapy delivery devices, such as capacitors, defibrillator electrodes, pacing electrodes, or mechanical chest compression devices, respirators, or medication delivery devices to the processor 218. It is appreciated that the functionality of the therapy delivery interface 202 can be incorporated into the sensor interface 212 to form a single interface coupled to the processor 218.

In addition, the components of the network interface 206 can couple the processor 218 to a computer network via a networking device, such as a bridge, router, or hub. According to a variety of embodiments, the network interface 206 can support a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, IDP, DTN, HTTP, FTP, SNMP, CDMA, NMEA, and GSM. It is appreciated that the network interface 106 of the medical device controller 200 can enable communication between other medical device controllers within a certain range.

To ensure data transfer is secure, in some embodiments, the medical device controller 200 can transmit data via the network interface 206 using a variety of security measures including, for example, TLS, SSL or VPN. In other embodiments, the network interface 206 can include both a physical interface configured for wireless communication and a physical interface configured for wired communication. According to various embodiments, the network interface 206 can enable communication between the medical device controller 200 and a variety of personal electronic devices including computer enabled glasses and earpieces. In one embodiment, the network interface 206 is also capable of transmitting and/or receiving information to assist in medical device location determination. Exemplary methods in which the network interface 206 can be used to assist in medical device location determination is described in U.S. Patent Application Publication No. 2014/0379255, titled "SYSTEMS AND METHODS OF DETERMINING LOCATION USING A MEDICAL DEVICE," published on Dec. 25, 2014, which is incorporated herein by reference in its entirety.

The components of the second sensor interface 214 can couple the processor 218 to one or more second sensors. These one or more second sensors can include dedicated biometric sensors, or other types of sensors that, in addition to performing other functions, can also function as biometric sensors. Biometric sensors can include one or more fingerprint sensors or scanners, palm print sensors or scanners, iris sensors or scanners, sensors or retinal scanners, DNA sensors, facial recognition sensor or scanner, voice recognition sensor and/or other biometric sensors. In certain embodiments, a combination of two or more of any of the above mentioned biometric sensors may be utilized in a single device to ensure identification accuracy. Biometric sensors can be integrated into the same housing as medical device controller 200. In other embodiments, biometric sensors can be detachably coupled to the second sensor interface 214 using wired connections (e.g., electrical or optical data leads) or wireless connections (e.g., using RFID, NFC, Bluetooth, or infrared communication links). Biometric sensors can comprise the biometric sensor on a smartphone, such as an Apple iPhone 5S, 6, 6S, or 6S Plus, which is communicably coupled with second sensor interface 214. Biometric sensors can also be dynamically attached or detached with second sensor interface 214. In some embodiments, second sensor interface 214 can be configured to automatically detect nearby devices incorporating biometric sensors, and to "pair" with said devices by establishing a secure wireless link. By automatically searching for and pairing with biometric sensors, second sensor interface 214 can obviate any need for EMS caregivers to spend time configuring or setting up the biometric functionality of the medical device. Using second sensor interface 214, the medical device controller 200 can be configured to take and/or store a biometric signature associated with a patient and/or a caregiver at the same time, and/or during the same medical event or medical encounter, as when the medical device controller 200 is (i) measuring and/or storing a physiological parameter associated with a patient through sensor interface 212, and/or (ii) delivering a patient treatment through therapy delivery interface 202.

The user interface 208 shown in FIG. 2 can include a combination of hardware and software components that allow the medical device controller 200 to communicate with an external entity, such as a patient or other user. These components may be configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens, and speakers. In some embodiments, the electrodes include an illuminating element, such as an LED. In other embodiments, the printing devices include printers capable of rendering visual or tactile (Braille) output.

Thus, the various system interfaces incorporated in the medical device controller 200 allow the device to interoperate with a wide variety of devices in various contexts. For instance, some embodiments of the medical device controller 200 are configured to perform a process of sending critical events and data to a centralized server via the network interface 206. An illustration of a process in accord with these embodiments is disclosed in U.S. Pat. No. 6,681,003, titled "DATA COLLECTION AND SYSTEM MANAGEMENT FOR PATIENT-WORN MEDICAL DEVICES," and issued on Jan. 20, 2004, which is incorporated herein by reference in its entirety.

Various components in FIG. 2 are optional and may not be included in every embodiment. For instance, a heart rate monitor may employ the medical device controller 200 to issue alarms but may not necessarily include a therapy delivery interface 202 to treat cardiac abnormalities. Similarly, an ambulatory defibrillator may include the medical device controller 200 to provide alarm functionality but may not necessarily include a network interface 206, where, for example, the ambulatory defibrillator is designed to rely on the user interface 208 to announce alarms.

The medical device controller 200 has a variety of potential applications and is well suited to devices that notify external entities of a variety of events, some of which may require a predetermined response from the external entity. Predetermined responses can include any response that is appropriate given the event being reported. Predetermined responses can include acknowledgment of the alarm, entry of information indicating that the alarm is being addressed and rectification of the event or condition that triggered the alarm. Examples of devices to which the medical device controller 200 is well suited include critical care medical devices, such as a wearable ambulatory external defibrillator, an Automated External Defibrillator (AED), or a mechanical chest compression or resuscitation assistance device, such as the Autopulse® system from ZOLL Medical Corporation of Chelmsford, Mass.

Embodiments of the present disclosure may be used with and/or embodied by one or more devices, for example one or more medical devices. Medical devices according to some embodiments of the present disclosure include, without limitation, patient monitoring and/or treatment devices cardiopulmonary resuscitation (CPR) assistance devices, such as mechanical or automated chest compression devices and manual cardiopulmonary resuscitation (CPR) assistance devices, ventilation devices, aspirators and fluid resuscitation devices. Patient monitoring and/or treatment devices include, without limitation, defibrillators, monitors, and/or AEDs, and portable or wearable versions thereof, for example the ZOLL® R Series®, X Series®, M Series®, Propaq MD, Propaq M, LifeVest®, as well as related electrodes, batteries, and/or accessories, according to embodiments of the present disclosure. Mechanical and/or automated chest compression devices include, without limitation, automatic mechanical chest compression devices (such as the ZOLL® AutoPulse® device) and/or mechanically controlled chest compression devices (such as the Physio Control LUCAS device). Manual CPR or CPR assistance devices include, without limitation, intrathoracic pressure regulation (IPR) devices, including impedance threshold devices (ITDs) (such as the ZOLL® ResQGARD and/or ResQPOD devices) and active compression-decompression CPR devices (such as the ZOLL® ResQPUMP device), cardiopumps, as well as electrode systems (such as ZOLL® CPR-D-Padz®, CPR-Stat-padz, and/or RealCPR Help® applications), according to embodiments of the present disclosure. Ventilation devices include, without limitation, ventilators (such as the ZOLL EMV+, AEV, Eagle II, and Eagle II MRI devices), according to embodiments of the present disclosure. Aspirators include, without limitation, Ultra-Lite® vacuum pump and Model 326, according to embodiments of the present disclosure. Fluid Resuscitation devices include, without limitation, the Power Infuser®, according to embodiments of the present disclosure. In certain embodiments, the above devices may include or be used in conjunction with a controller, computing device, sensors and/or memory capable of performing one or more of the various functionalities of the embodiments of the present disclosure.

Figure 3:
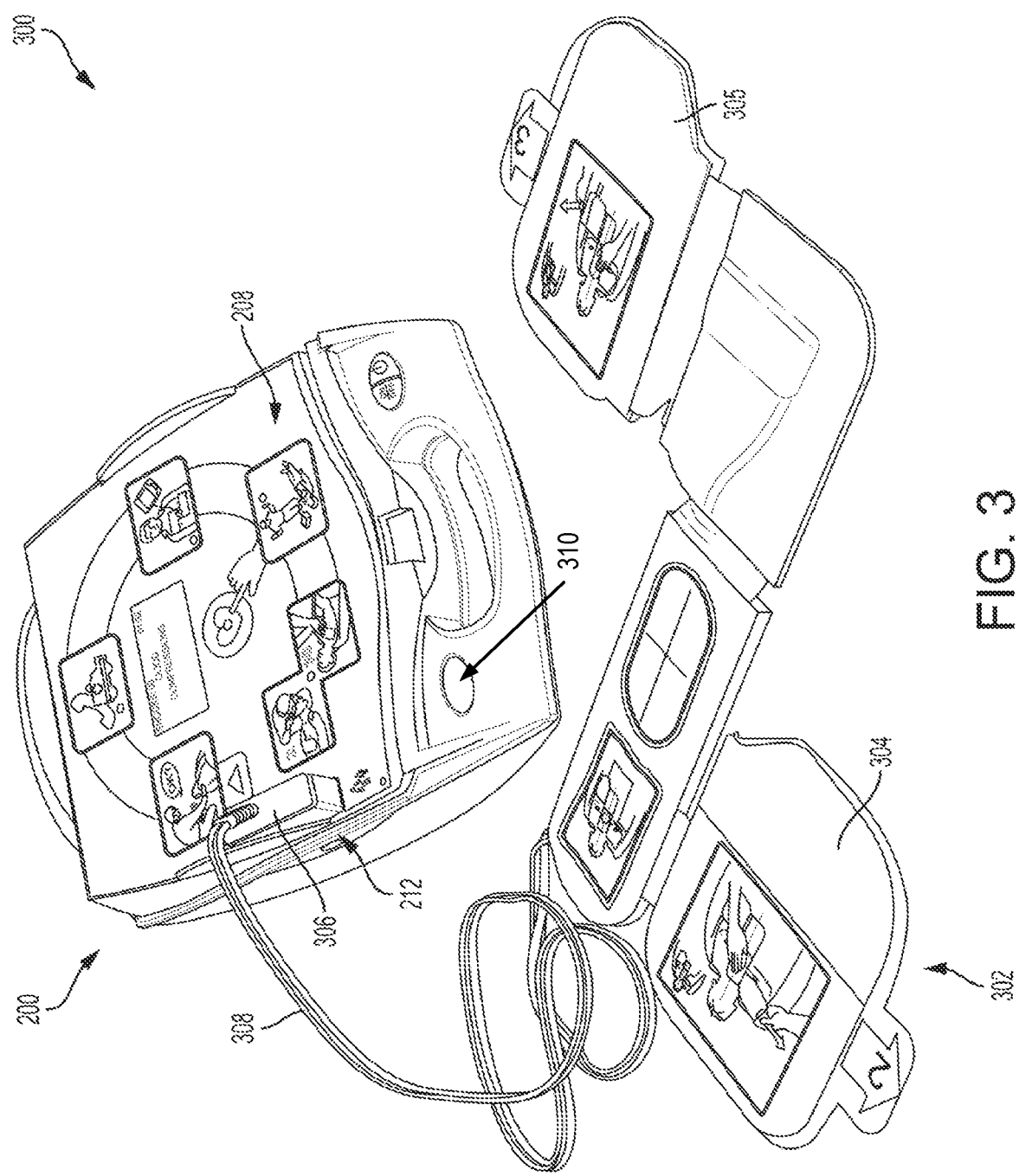
FIG. 3 illustrates an automated external defibrillator, according to some embodiments.

In one exemplary embodiment, the medical device controller 200 can be implemented within or in conjunction with an Automated External Defibrillator (AED). AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED, in addition, may be configured to provide counseling to an operator as to how to perform cardiopulmonary resuscitation (CPR). FIG. 3 illustrates an AED available from ZOLL Medical Corporation of Chelmsford, Mass. As shown, the AED 300 includes a medical device controller 200 and an electrode assembly 302.

The electrode assembly 302 includes one or more sensing electrodes 304 (e.g., ECG sensors), one or more therapy electrodes 305 (e.g., defibrillation pads), a connector 306, wiring 308 electrically coupling the connector 306 to the one or more sensing electrodes 304 and one or more therapy electrodes 305. As shown in FIG. 3, the connector is configured to couple the electrode assembly 302 to the medical device controller 200 and, more specifically, the one or more sensing electrodes to the sensor interface 212 and the one or more therapy electrodes to the therapy delivery interface 202.

The medical device controller 200 of the AED 300 is configured to detect the cardiac rhythm of the patient and provide defibrillating shocks to the patient as appropriate. The user interface 208 of the AED 300 may include a variety of components configured to communicate with the operator including, but not limited to, a display screen, a speaker, and one or more buttons. In this embodiment, the AED 300 includes a display screen to display notifications to an operator. The notifications may provide instructions to the operator regarding the proper administration of CPR to the patient. The notifications on the display may be accompanied by audible alerts from the speaker to further assist the operator in administering CPR to the patient.

AED 300 can also comprise a biometric sensor 310, shown here as a fingerprint scanner. Biometric sensor 310 can be communicably coupled to second sensor interface 214 of medical device controller 200. As discussed previously, in some embodiments, biometric sensor 310 can be coupled to the housing of the medical device using a wired connection or a wireless connection. Biometric sensor 310 can also be combined with other physiological sensors, such as a blood oxygen $SpO_2$ sensor that clips onto a finger of a patient. In some embodiments, biometric sensor 310 can also be integrated into a physical button, such that the sensor can automatically detect and record a user's fingerprint when the button is actuated.

In other embodiments, medical device controller 200 can be configured to control a wearable defibrillator that includes a garment (e.g., a vest or belt) that is worn by the patient. The wearable defibrillator monitors the patient's ECG with sensing electrodes, detects life threatening arrhythmias, and delivers a cardioverting or defibrillating shock through the therapy pads if treatment is necessary. An example of a wearable defibrillator is described in greater detail in U.S. Patent Application Publication No. US 2014/0379255, titled "SYSTEMS AND METHODS OF DETERMINING LOCATION USING A MEDICAL DEVICE", published Dec. 25, 2014, the entire contents of which is incorporated by reference. Such a wearable defibrillator can also comprise a biometric sensor that is either integrated into the harness or user interface, or coupled wirelessly or via a wired connection to the device's controller.

Figure 4:
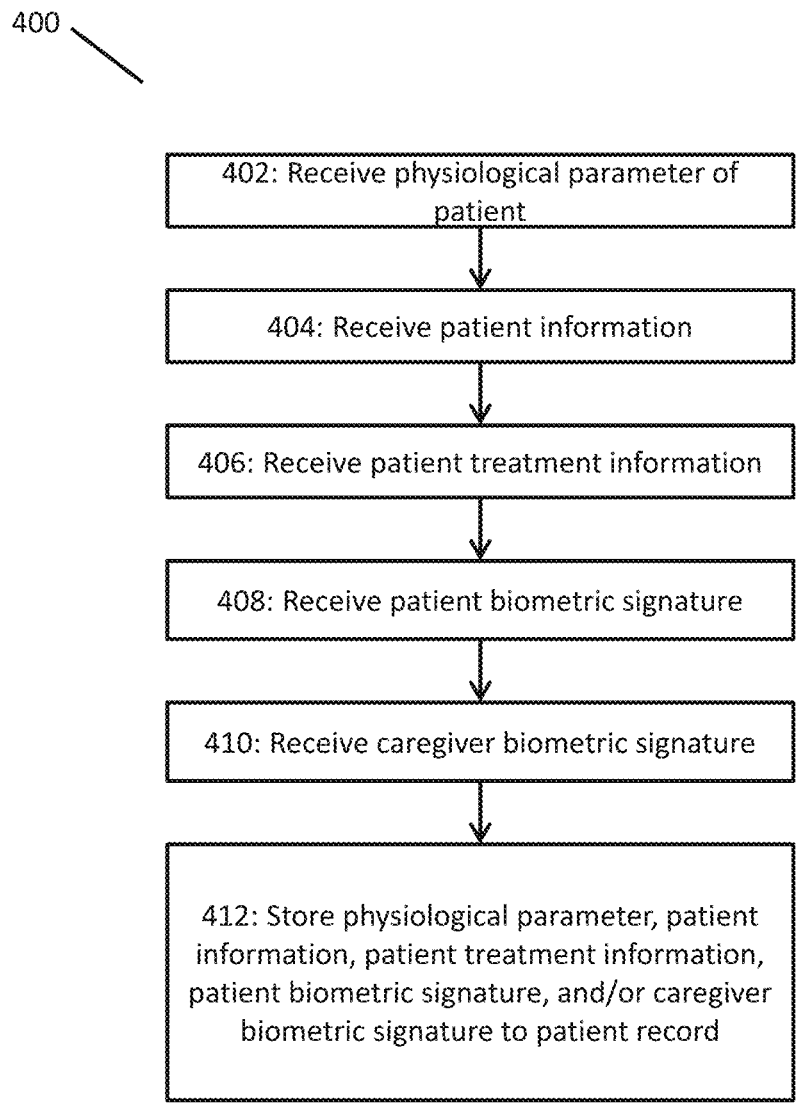
FIG. 4 illustrates an exemplary process for adding patient and/or caregiver biometric signatures into a patient record, according to some embodiments.

FIG. 4 illustrates an exemplary process 400 for adding patient and/or caregiver biometric signatures into a patient record. In some embodiments, process 400 can be implemented by medical device controller 200. For example, process 400 can be implemented at processor 218 in conjunction with data storage 204. At stage 402, process 400 can receive one or more physiological parameters of the patient. Physiological parameters can be received from sensor interface 212, and can include parameters such as body temperature, respiration rate, ECG traces, blood-oxygen data, heart rate, blood pressure, end-tidal $CO_2$ data, and the like.

At stage 404, process 400 can receive patient information. Patient information can comprise at least one of a medical condition, a medical history, and biographical information associated with the patient. Examples of medical conditions include diseases or abnormalities that the patient is believed to currently suffer from, such as diabetes, cancer, AIDS, or heart disease. Examples of medical history can include previous medical conditions that the patient has or continues to be afflicted with, as well as medical history related to family members of the patient. Biographical information can include information such as the patient's name, gender, age, address, patient identification number, and/or social security number. In some embodiments, this patient information can be received via user interface 208 if a user, such as a caregiver, types, dictates, or otherwise provides this information. In some embodiments, this patient information can be received via network interface 206, such as if a patient record is retrieved from a remote database of patient records, or via a computer-aided dispatch system.

At stage 406, process 400 can receive patient treatment information. This information can comprise a treatment that the patient has received, is currently receiving, or is expected to receive within a time period, such as during an emergency encounter. Examples of patient treatment information can include information regarding administration of medication (e.g., what medication, when administered, and at what dosage), information regarding an administration of a defibrillating electric shock (e.g., when administered, at what energy level), and/or information regarding an administration of a pacing electric shock (e.g., when administered, at what energy level). In some embodiments, patient treatment information can be received via therapy delivery interface 202 if the medical device controller 200 is also being used to deliver the patient treatment. In some embodiments, patient treatment information can also be received via user interface 208 if a user (e.g., a caregiver) provides this information, and/or via network interface 206 if another device, communicably coupled to medical device controller 200 via a network, provides the information.

At stage 408, process 400 can receive a patient biometric signature. As described above, the patient biometric signature can comprise, for example, one or more fingerprints, palm prints, iris scans, retinal scans, facial recognition scans, voice/voiceprint recognition or identification data and/or DNA profiles associated with the patient. In certain embodiments, a combination of two or more of any of the above mentioned biometric signatures can be collected, e.g., during the course of an emergency encounter or in a non-emergency setting, to ensure the accuracy of the patient identification. This patient biometric signature can be received via second sensor interface 214.

At stage 410, process 400 can receive a caregiver biometric signature. The caregiver biometric signature can comprise any of the biometric signature types of the patient biometric signature, and can also be received via second sensor interface 214. In one embodiment the same biometric sensor is capable of detecting both the caregiver biometric signature and the patient biometric signature; in another embodiment, the caregiver biometric signature is detected with a biometric sensor that is different from the biometric sensor that is used to detect the patient biometric signature.

At stage 412, process 400 can save the received physiological parameter, the received patient information, the patient treatment information, the patient biometric signature, and/or the caregiver biometric signature into a patient record, such as patient record 216 stored in data storage 204. By storing this information in conjunction with a patient biometric signature and/or a caregiver biometric signature, process 400 facilitates later identification of the patient and/or the caregiver, matching of the patient record with other records pertaining to the patient and/or caregiver, as well as population-wide analysis or audits of patient and/or caregiver records.

Process 400 can be modified by removing, adding, or rearranging any of the aforementioned stages. For example, process 400 can be modified by removing stage 402, such that the patient record does not contain physiological parameter data. Process 400 can also be modified by removing stage 404, such that the patient record does not contain biographical or medical history data. Process 400 can also be modified by removing stage 406, such that the patient record does not contain patient treatment information. Process 400 can also be modified by removing one of stages 408 or 410, such that the patient record contains only a patient biometric signature, or a caregiver biometric signature, but not both. Process 400 can also be modified by duplicating stages 408 or 410, such that multiple patient biometric signatures or multiple caregiver biometric signatures are taken and included in the patient record. Multiple patient biometric signatures can be recorded and included for redundancy purposes and to further assure correct identification of a patient. Multiple caregiver biometric signatures can also be recorded for similar redundancy purposes. Alternatively, multiple caregiver biometric signatures corresponding to multiple caregivers can be recorded. This can be used to record some or all caregivers that treated a patient during a time period (such as during an emergency encounter). Process 400 can also be modified by rearranging stages 402, 404, 406, 408, and/or 410 so that they are performed in any arbitrary order.

Furthermore, process 400 can also be modified by adding additional stages. For instance, process 400 can further include a step in which process 400 determines whether a set of records stored in memory already includes one or more matching records associated with one or more patient biometric signatures that correspond to the received patient biometric signature. If no matching records are identified, process 400 can create a new patient record. If one or more matching records are identified, process 400 can merge the matching records into one record, and/or add the received physiological parameter data, patient information data, and/or patient treatment information into one or more of the matching records.

In some embodiments, process 400 can be executed every time a new patient record is created. For example, a medical device controller executing process 400 can create a new emergency encounter record for every emergency encounter. As discussed above, an "emergency encounter record" can comprise a patient record that relates to an emergency encounter. Also as discussed above, an emergency encounter record can also comprise a record of an emergency medical services (EMS) encounter that relates to an EMS call or visit pertaining to a particular patient. A medical device controller executing process 400 can create a new emergency encounter record for every EMS encounter, and record the patient's physiological parameters, patient information, patient treatment information, and biometric signatures pertaining to one or both of the patient and caregiver during the same encounter. This recorded information can be added to an emergency encounter record pertaining to a particular EMS encounter or patient.

In some embodiments, process 400 can be executed multiple times to update a single patient record with multiple patient and/or caregiver biometric signatures. In some embodiments, process 400 can also be executed once for multiple patient records—in these embodiments, a single set of patient and/or caregiver biometric signatures can be applied to multiple patient records.

Figure 5:
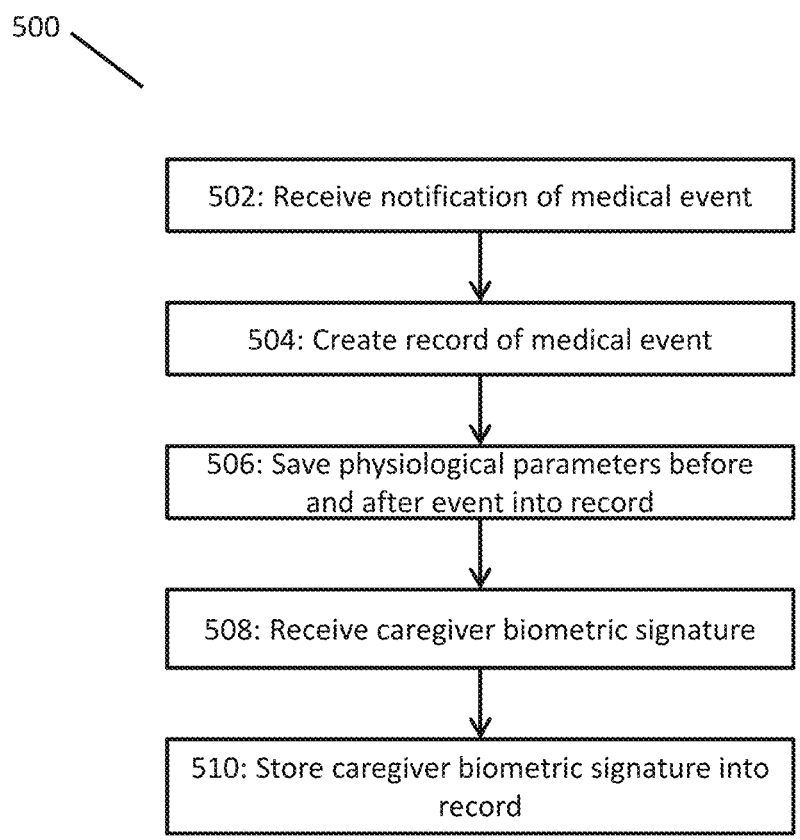
FIG. 5 illustrates an exemplary process for adding caregiver biometric signatures to records of medical events in a patient record, according to some embodiments.

FIG. 5 illustrates an exemplary process 500 for adding caregiver biometric signatures to records of medical events in a patient record. As used herein, medical events can refer to events that occur at discrete times, and that signify a medical data point in the patient's record. Medical events can include the status of a patient physiological parameter at a particular time (e.g., a blood pressure reading, an ECG trace, a temperature reading), an administration of medication or treatment, a medical examination or assessment, and/or an update to the patient record to modify the patient's biographical information, medical information, medical history information, and the like. Medical events can also include medically significant events. As used herein, medically significant events can refer to events that occur at discrete times, and that signify a medically significant development in the patient's condition or treatment. For instance, medically significant events can refer to an administration of medication such as epinephrine or adenosine, an administration of a defibrillating electric shock, an administration of a pacing electric shock, a transmission of an electrocardiogram (ECG) to a remote facility (such as a receiving hospital), a cardiac arrest event, a stroke, a seizure, an endotracheal intubation, an administration of cardiopulmonary resuscitation (CPR), a time of death, and the like.

At stage 502, process 500 can receive a notification of a medical event. In some embodiments, the notification can be received via user interface 208. For instance, the user interface can detect an actuation of a physical or touchscreen button. Alternatively, the user interface can recognize a vocal cue detected by a microphone, and/or recognize a visual gesture from a caregiver recorded by a video sensor. Examples of ways in which the user interface can update a patient record based on visual gestures or actions of a caregiver recorded by a video sensor can be found in U.S. Patent Application Publication No. 2014/0096091 published Apr. 3, 2014, entitled "SYSTEMS AND METHODS FOR THREE-DIMENSIONAL INTERACTION MONITORING IN AN EMS ENVIRONMENT," the entire contents of which are incorporated by reference herein. Process 500 can be configured to recognize multiple types of medical events, and different user input, such as actuation of different buttons, can result in notification of different medical events.

At stage 504, process 500 can create a record of the medical event in the patient record. The record of the medical event can comprise a time stamp at which the medical event occurred. The record of the medical event can also optionally comprise various detailed information regarding the event. For instance, if the medical event is an administration of medication, the record of the event can reflect the type of medication administered and the dosage. If the medical event is an administration of an electric shock, the record of the event can reflect the number of shocks, and/or the voltage level of the shock.

At stage 506, process 500 can save into the event record measured physiological parameters of the patient for a pre-determined time period immediately before the medical event, and/or for a pre-determined time period immediately after the medical event. For example, process 500 can save the patient's observed heart rate, blood pressure, $SpO_2$ levels, end-tidal $CO_2$ levels, and/or ECG trace immediately before and immediately after the medical event. This creates a "snapshot" of the patient's condition immediately before and/or after the medical event. Such "snapshots" can be analyzed to determine the effect of a medical event on a patient's condition. For instance, by measuring a patient's ECG trace or heart rate immediately before and after a defibrillator shock, or immediately before and after an administration of epinephrine, the event record can facilitate determination of the effectiveness of the defibrillator shock and/or epinephrine. Stage 506 is optional and need not be included; furthermore, some embodiments of stage 506 can record physiological parameters only before or only after a medical event (as opposed to both before and after).

At stage 508, process 500 can receive a caregiver biometric signature. The caregiver biometric signature can be received in ways similar to that described above in relation to FIG. 4. At stage 510, the caregiver biometric signature can be inserted into the record of the medical event. By associating the caregiver biometric signature with the medical event, process 500 can facilitate later audits or analysis of patient records to ensure compliance with rules and regulations. For instance, caregiver biometric signatures in event records can be used to ensure that only appropriately qualified caregivers (e.g., doctors or paramedics) administer certain types of treatments (e.g., defibrillating shocks). Analysis of multiple event records having caregiver biometric signatures can also be used identify high-performing caregivers, such as for promotion or compensation purposes, or to identify under-performing caregivers, such as for additional training purposes.

Process 500 can also be modified by removing, adding, or rearranging any of the aforementioned stages. For example, process 500 can be modified such that stage 508 is performed at any time throughout process 500. In some embodiments, the caregiver biometric signature is received once, at the beginning of a particular time period, such as an emergency encounter. All medical events that take place during that time period can automatically be associated with that caregiver biometric signature. In some embodiments, there can be multiple time periods during an emergency encounter, such as when the patient is handed off between multiple caregivers over the course of the encounter. In this case, each caregiver can "log in" when he or she assumes responsibility for the patient by providing his or her biometric signature. In some embodiments, a different caregiver biometric signature is received for every medical event. For example, some or all types of medical events can require input of a caregiver biometric signature before the event can be recorded. In some embodiments, a caregiver biometric signature can be required to authenticate a caregiver, and to ensure that a caregiver has the appropriate training and/or credentials to authorize or unlock a certain type of patient treatment (e.g., a defibrillator shock). In some embodiments, process 500 can permit notification and recording of a medical event, and then request and receive a caregiver biometric signature after the event has transpired. In yet other embodiments, a biometric sensor can be integrated into the user interface used to notify process 500 regarding a medical event. For instance, a fingerprint sensor can be integrated into a button used to notify a medical event, such that actuation of the button automatically causes the fingerprint sensor to detect and record the caregiver's biometric signature. Other types of biometric sensors can also be used, such that a detection of the caregiver's biometric signature automatically signifies that a medical event has transpired.

Figure 6:
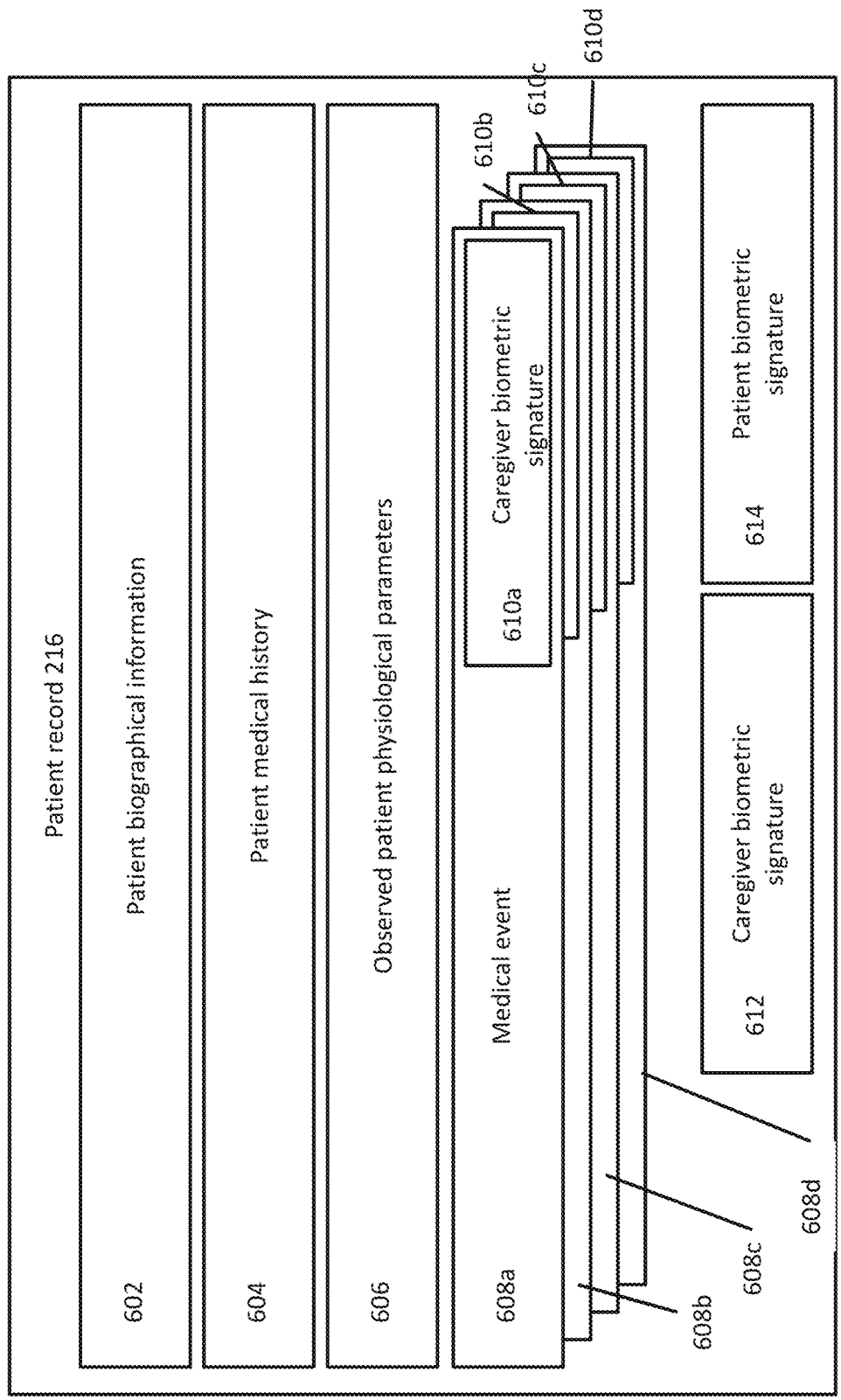
FIG. 6 is a conceptual block diagram illustrating the components of an exemplary patient record, according to some embodiments.

FIG. 6 is a conceptual block diagram illustrating the components of an exemplary patient record 216, according to some embodiments. The patient record 216 can comprise patient biographical information 602, patient medical history 604, and observed patient physiological parameters 606. The patient biographical information 602 can comprise some or all of the patient biographical information described above, the patient medical history 604 can comprise some or all of the patient medical history information described above, and the patient physiological parameters 606 can comprise some or all of the physiological parameters described above. The patient record 216 can also comprise a plurality of records of medical events 608*a-d*. In some embodiments, each medical event can be associated with a caregiver biometric signature, illustrated as elements 610*a-d*. Alternatively or in addition, patient record 216 can also include one or more caregiver biometric signatures that are not associated with any medical events (e.g., caregiver biometric signature 612). This caregiver biometric signature can, for example, be associated with a primary caregiver that had overall responsibility for the care of the patient. Patient record 216 can also include patient biometric signature 614 that uniquely identifies the patient. As described above, patient biometric signatures and/or caregiver biometric signatures can be recorded by a medical device every time the device creates a patient record. Patient and/or caregiver biometric signatures can also be recorded many times by a medical device for each patient record. In addition, the medical device can also be configured to record a patient and/or caregiver biometric signature once for a series of patient records—in such cases, the device can apply a single set of patient and/or caregiver biometric signatures to multiple patient records.

Patient record 216 can be stored in data storage 204 of medical device controller 200, as illustrated in FIG. 2. Alternatively or in addition, patient record 216 can also be stored in enterprise storage server 126. The contents of patient record 216 can be requested and accessed via enterprise workstation 122 and/or administration workstation 132, potentially through a connection hosted or facilitated by enterprise application server 128. The contents of patient record 216 can also be requested and accessed by devices within mobile environment 101, such as devices 104, 106, 108, and/or 110 in FIG. 1. For instance, patient records stored on enterprise storage server 126 can be queried for all patient records associated with a certain caregiver, or a certain set of caregivers, or for caregivers who satisfy certain criteria (e.g., training level, experience, geographic location).

Figure 7:
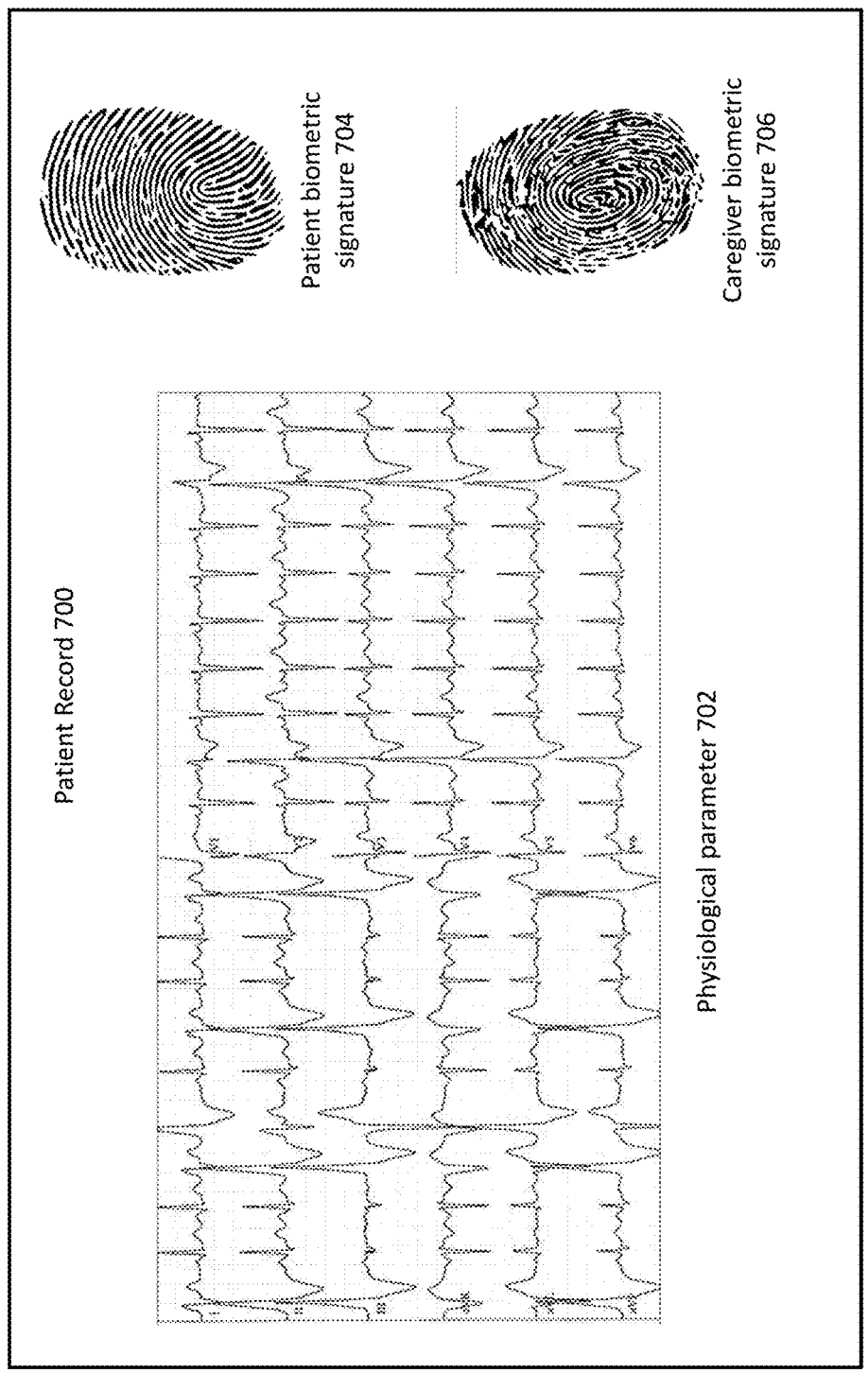
FIG. 7 is another conceptual block diagram illustrating the components of an exemplary patient record, according to some embodiments.

FIG. 7 is another conceptual block diagram illustrating another exemplary embodiment of patient record 700, according to some embodiments. In some cases, patient record 700 can comprise all or part of patient record 216 in FIG. 2. Patient record 700 can include a record of a physiological parameter 702 of a patient. The physiological parameter 702 is illustrated in FIG. 7 as comprising an electrocardiogram (ECG) trace, but can also comprise any other type of physiological parameter. Non-limiting examples of physiological parameters can include a patient's heart rate, temperature, respiratory rate, blood oxygen level, blood pressure, end-tidal carbon dioxide levels, and/or the like. Patient record 700 can also include one or both of a patient biometric signature 704 and a caregiver biometric signature 706. Both types of biometric signatures are illustrated in FIG. 7 as comprising an image of a fingerprint, but other types of biometric signatures are also possible, as described herein. Furthermore, instead of an image of a fingerprint, biometric signatures can also comprise data derived from a fingerprint, such as a unique alphanumeric string or set of numbers derived from a fingerprint. In some cases, the contents of patient record 700, including both the patient physiological parameter and the patient and/or caregiver biometric signature, can be displayed on an output screen simultaneously. Keeping the patient and/or caregiver biometric signature on the same patient record as the patient physiological data can facilitate easy identification and tracking of the patient record.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical device for providing defibrillation therapy and patient monitoring, the medical device comprising:
   a housing;
   a therapy delivery interface disposed within the housing;
   at least one first sensor interface disposed within the housing, communicably coupled to at least one physiological sensor, and configured to measure at least one physiological parameter of a patient based on signals received from the at least one physiological sensor;
   at least one second sensor interface disposed within the housing, communicably coupled to at least one biometric sensor, and configured to detect biometric signatures based on signals received from the at least one biometric sensor;
   a data interface, disposed within the housing, configured to receive a first patient encounter record from at least one other device for therapy delivery, wherein the first patient encounter record (i) relates to use of the at least one other device for therapy delivery during an emergency encounter with the patient, and (ii) includes a first patient biometric signature;
   at least one memory disposed within the housing; and
   a control system disposed within the housing and communicably coupled to the at least one first sensor interface, the at least one second sensor interface, the therapy delivery interface, the data interface, and the at least one memory, the control system comprising a processor configured to:
   receive, from the at least one other device for therapy delivery, via the data interface, the first patient encounter record;
   store the first patient encounter record in the at least one memory;
   receive the at least one physiological parameter of the patient during the emergency encounter;
   receive a second patient biometric signature that is detected by the at least one second sensor interface;
   receive a caregiver biometric signature that is detected using the at least one second sensor interface;
   record in a second patient encounter record that is stored in the at least one memory, and that relates to use of the medical device during the emergency encounter:
      (a) at least one medical event associated with the emergency encounter, the at least one medical event comprising a delivery of therapy to the patient via the therapy delivery interface,
      (b) the at least one physiological parameter of the patient measured by the at least one first sensor interface during the emergency encounter, and
      (c) the second patient biometric signature that is detected by the at least one second sensor interface;
   make a determination, by the processor included in the control system disposed within the housing, that the first patient biometric signature included in the first patient encounter record corresponds to the second patient biometric signature detected by the at least one second sensor interface; and
   in response to making the determination, merge the first patient encounter record and the second patient encounter record into a merged record for the emergency encounter that relates to use of both the medical device and the at least one other device for therapy delivery during the emergency encounter.

2. The medical device of claim 1, wherein the at least one second sensor interface is configured to detect the second patient biometric signature during the emergency encounter and the at least one first sensor interface is further configured to measure the at least one physiological parameter of the patient during the emergency encounter.

3. The medical device of claim 2, wherein the at least one second sensor interface is configured to detect the second patient biometric signature at a same time as when the at least one first sensor interface is measuring the at least one physiological parameter of the patient.

4. The medical device of claim 1, wherein the data interface is configured to receive patient information regarding a medical condition, a medical history, and/or biographical information associated with the patient, wherein the merged record further comprises the patient information.

5. The medical device of claim 4, wherein the medical device comprises a patient monitor/defibrillator communicatively coupled to a tablet computing device.

6. The medical device of claim 5, wherein the data interface is configured to receive the patient information from a remote patient record database.

7. The medical device of claim 6, wherein the data interface is configured to receive the patient information via a computer-aided dispatch system.

8. The medical device of claim 7, wherein the patient information comprises one or more of patient name, gender, age, address, patient identification number, and social security number.

9. The medical device of claim 1, further comprising a wireless interface configured to communicate with a database at a remote location, wherein the control system is further configured to:
send at least one of the first and second patient biometric signatures to the database, and
retrieve, from the database, medical record and/or biographical information associated with the patient.

10. The medical device of claim 1, wherein the control system is further configured to
determine if the at least one memory is storing an additional emergency encounter record comprising a third patient biometric signature that corresponds to the first patient biometric signature, and
further merge the merged record with the additional emergency encounter record.

11. The medical device of claim 1, further comprising:
a scanner configured to scan a piece of personal identification associated with the patient to determine scanned patient information, wherein the control system is further configured to comprise the scanned patient information in the merged record.

12. The medical device of claim 1, wherein the at least one biometric sensor comprises a fingerprint sensor, a palm sensor, an iris sensor, a retinal sensor, a facial recognition sensor and/or voice recognition sensor.

13. The medical device of claim 1, wherein the at least one physiological sensor comprises an electrocardiogram (ECG) sensor, a heartbeat sensor, a blood oxygen sensor, an end-tidal carbon dioxide sensor, and/or an ultrasound sensor.

14. The medical device of claim 1, wherein the device comprises one of a patient monitor/defibrillator configured to deliver a therapeutic electric shock to the patient, an Automated External Defibrillator (AED), and a wearable defibrillator.

15. The medical device of claim 1, wherein the at least one physiological sensor is a blood oxygen sensor configured to fit over a finger of the patient and the at least one biometric sensor is a fingerprint scanner disposed on the blood oxygen sensor.

16. The medical device of claim 1, wherein the at least one biometric sensor is communicably coupled to the at least one second sensor interface via a wireless connection.

17. The medical device of claim 16, wherein the at least one biometric sensor is part of a smartphone.

18. The medical device of claim 1, further comprising a user interface configured to accept user input comprising patient information, wherein the user interface is communicably coupled to the control system and wherein the merged record further comprises the patient information.

19. The medical device of claim 18, the patient information comprising information regarding a medical condition, a medical history, and/or biographical information associated with the patient.

20. The medical device of claim 1, wherein the therapy delivery interface is configured to couple to one or more defibrillation therapy electrodes and the delivery of therapy to the patient comprises a delivery of defibrillation therapy.

21. The medical device of claim 1, wherein a single multipurpose interface provides functionality associated with the therapy delivery interface and the first sensor interface.

22. The medical device of claim 1, wherein the control system is further configured to:
make a second determination that a caregiver biometric signature included in the first patient encounter record corresponds to the caregiver biometric signature that is detected using the at least one second sensor interface.

23. The medical device of claim 1, further comprising a wireless interface configured to communicate with a database at a remote location, wherein the control system is further configured to:
query the database at the remote location for patient records associated with a certain caregiver, and
receive a previously saved emergency encounter record based on the second patient biometric signature and the caregiver biometric signature.

24. The medical device of claim 1, wherein the at least one other device for therapy delivery comprises one or more of a patient monitor/defibrillator configured to deliver a therapeutic electric shock to the patient, an Automated External Defibrillator (AED), a wearable defibrillator, a cardiac monitoring device, a ventilator, and a mechanical chest compression device.

* * * * *